United States Patent
Xia et al.

(10) Patent No.: US 11,829,407 B2
(45) Date of Patent: Nov. 28, 2023

(54) SYSTEMS AND METHODS FOR FILE ARCHIVING

(71) Applicant: WUHAN UNITED IMAGING HEALTHCARE CO., LTD., Hubei (CN)

(72) Inventors: Chao Xia, Wuhan (CN); Xing Ming, Wuhan (CN); Yaguang Wang, Wuhan (CN); Dingxin Wang, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 0 days.

(21) Appl. No.: 17/452,783

(22) Filed: Oct. 29, 2021

(65) Prior Publication Data

US 2022/0138248 A1 May 5, 2022

(30) Foreign Application Priority Data

Oct. 29, 2020 (CN) .......................... 202011185170.3
Nov. 5, 2020 (CN) .......................... 202011222321.8
Dec. 10, 2020 (CN) .......................... 202011435223.2

(51) Int. Cl.
*G06F 16/535* (2019.01)
*G06F 16/538* (2019.01)
(Continued)

(52) U.S. Cl.
CPC ............ *G06F 16/535* (2019.01); *G06F 16/51* (2019.01); *G06F 16/538* (2019.01); *G06F 16/58* (2019.01)

(58) Field of Classification Search
CPC ...... G06F 16/535; G06F 16/51; G06F 16/538; G06F 16/58; G16H 30/20
See application file for complete search history.

(56) References Cited

U.S. PATENT DOCUMENTS 5,828,814 A * 10/1998 Cyman .................. G06K 15/02
358/1.13
6,246,804 B1 6/2001 Sato et al.
(Continued)

FOREIGN PATENT DOCUMENTS

CN 106850758 A 6/2017
CN 107180199 A 9/2017
(Continued)

OTHER PUBLICATIONS

First Office Action in Chinese Application No. 202011185170.3 dated Jan. 20, 2022, 8 pages.
(Continued)

*Primary Examiner* — Angelica Ruiz
(74) *Attorney, Agent, or Firm* — METIS IP LLC

(57) ABSTRACT

Systems and methods for file archiving. The systems may obtain an image file to be transmitted that includes image data in a first format and a metadata file in a second format. The metadata file may include identification information of the image data. The image data may be acquired from a scan of a subject using an imaging device. The systems may transmit, according to a first protocol, the image data in the first format to an image archiving system for archiving. The systems may also transmit, according to a second protocol, the metadata file in the second format to the image archiving system for archiving.

20 Claims, 11 Drawing Sheets

(51) Int. Cl.
*G06F 16/51* (2019.01)
*G06F 16/58* (2019.01)

(56) References Cited

U.S. PATENT DOCUMENTS

| | | | |
|---|---|---|---|
| 6,954,802 B2* | 10/2005 | Sutherland | G16H 30/20 |
| | | | 710/5 |
| 9,235,889 B1* | 1/2016 | Frenkel | G06T 1/60 |
| 10,257,174 B2* | 4/2019 | Rosenberg | H04L 63/0876 |
| 2001/0019587 A1 | 9/2001 | Hashimoto et al. | |
| 2001/0051881 A1* | 12/2001 | Filler | G16H 40/67 |
| | | | 705/3 |
| 2006/0206547 A1 | 9/2006 | Kulkarni et al. | |
| 2006/0256380 A1 | 11/2006 | Klassen et al. | |
| 2007/0064981 A1 | 3/2007 | Meijer | |
| 2007/0076961 A1 | 4/2007 | Shiiyama | |
| 2011/0282844 A1 | 11/2011 | Bates et al. | |
| 2014/0254934 A1 | 9/2014 | Laxminarayana Bhat et al. | |
| 2016/0125135 A1 | 5/2016 | Ramanathan et al. | |
| 2017/0206331 A1* | 7/2017 | Veliah | G16H 10/60 |
| 2019/0095478 A1 | 3/2019 | Tankersley et al. | |
| 2020/0076578 A1 | 3/2020 | Ithal et al. | |
| 2020/0273559 A1* | 8/2020 | Yousfi | G06T 17/20 |
| 2020/0411164 A1 | 12/2020 | Donner | |

FOREIGN PATENT DOCUMENTS

| | | |
|---|---|---|
| CN | 109411056 A | 3/2019 |
| CN | 109710614 A | 5/2019 |
| CN | 109740366 A | 5/2019 |
| CN | 110570928 A | 12/2019 |
| CN | 110825698 A | 2/2020 |
| CN | 110990877 A | 4/2020 |
| CN | 111225375 A | 6/2020 |
| CN | 111739613 A | 10/2020 |

OTHER PUBLICATIONS

First Office Action in Chinese Application No. 202011222321.8 dated Jan. 21, 2022, 10 pages.
First Office Action in Chinese Application No. 202011435223.2 dated Apr. 1, 2022, 11 pages.
The Extended European Search Report in European Application No. 21205586.7 dated Mar. 21, 2022, 12 pages.
The Extended European Search Report in European Application No. 21205635.2 dated Mar. 23, 2022, 12 pages.
Medical Imaging & Technology Alliance: DICOM PS3.1 2019e—Part 1: Introduction and Overview, 2019, 34 pages.
Medical Imaging & Technology Alliance: DICOM PS3.4 2019e—Part 4: Service Class Specifications, 2019, 400 pages.
Medical Imaging & Technology Alliance: DICOM PS3.5 2019e—Part 5: Data Structures and Encoding, 2019, 150 pages.
Medical Imaging & Technology Alliance: DICOM PS3.6 2019e—Part 6: Data Dictionary, 2019, 248 pages.
Medical Imaging & Technology Allicance: DICOM PS3.7 2019e—Part 7: Message Exchange, 2019, 128 pages.
Medical Imaging & Technology Alliance: DICOM PS3.10 2019e—Part 10: Media Storage and File Format for Media Interchange, 2919, 50 pages.
Navid Alemi Koohbanani et al., NuClick: A Deep Learning Framework for Interactive Segmentation of Microscopy Images, arXiv: 2005.14511v2 [cs.CV], 2020, 16 pages.
K .-K. Maninis et al., Deep Extreme Cut: From Extreme Points to Object Segmentation, arXiv: 1711.09081v2 [cs.CV]. 2018, 10 pages.
Tomas Sakinis et al., Interactive Segmentation Of Medical Images Through Fully Convolutional Neural Networks, arXiv: 1903.08205v1 [cs.CV], 2019, 10 pages.
Rodrigo Benenson et al., Large-Scale Interactive Object Segmentation With Human Annotators, arXiv: 1903.10830v2 [cs.CV], 2019, 10 pages.
Guotai Wang et al., Interactive Medical Image Segmentation Using Deep Learning With Image-Specific Fine-tuning, IEEE Transactions On Medical Imaging, 2018, 12 pages.
Zihao Liu et al., Machine Vision Guided 3D Medical Image Compression for Efficient Transmission and Accurate Segmentation in the Clouds, arXiv: 1904.08487v1 [cs.CV], 2019, 10 pages.

* cited by examiner

SYSTEMS AND METHODS FOR FILE ARCHIVING

CROSS-REFERENCE TO RELATED APPLICATIONS

This application claims priority of Chinese Application No. 202011185170.3 filed on Oct. 29, 2020, Chinese Patent Application No. 202011222321.8 filed on Nov. 5, 2020, and Chinese Application No. 202011435223.2 filed Dec. 10, 2020, the contents of which are hereby incorporated by reference.

TECHNICAL FIELD

The present disclosure generally relates to the field of file management, and more particularly, relates to systems and methods for file transmission and archiving.

BACKGROUND

A Picture Archiving and Communication System (PACS) is a system configured to provide storage and access to image data (in the form of, e.g., images, raw data, etc.) from multiple modalities. The PACS is configured for massive storage of production of a variety of medical images digitally through a variety of interfaces. Image data can be accessed by retrieval from the PACS when needed under a certain authorization. In addition, the PACS may be configured with functions for auxiliary diagnostic management.

Currently, the PACS focuses on archiving medical images that are in a standard format (e.g., a Digital Imaging and Communications in Medicine (DICOM) format) of a limited size. For a file of a relatively large size, there may be a high risk of packet loss or other problems resulting in file transmission failure in the PACS. However, in practical applications, a medical device may generate a file of a non-standard format (e.g., raw data generated by the medical device) and a relatively large size (e.g., a size larger than 200 G) that needs to be transmitted to the PACS for archiving.

Therefore, it is desirable to provide a system and method for archiving, thereby effectively and reliably transmitting and archiving a large non-standard file.

SUMMARY

In one aspect of the present disclosure, a system is provided. The system may include at least one storage device including a set of instructions, and at least one processor configured to communicate with the at least one storage device. When executing the set of instructions, the at least one processor may be configured to direct the system to perform following operations. The operations may include obtaining an image file to be transmitted that includes image data in a first format and a metadata file in a second format. The metadata file may include identification information of the image data. The image data may be acquired from a scan of a subject using an imaging device. The operations may include transmitting, according to a first protocol, the image data in the first format to an image archiving system for archiving. The operations may also include transmitting, according to a second protocol, the metadata file in the second format to the image archiving system for archiving.

In some embodiments, the first format may be a non-standard format.

In some embodiments, the second format may be a self-defined format.

In some embodiments, the second format may be a self-defined Digital Imaging and Communications in Medicine (DICOM) format.

In some embodiments, the first protocol may be a proprietary file transmission protocol, and the second protocol may be a standard file transmission protocol.

In some embodiments, the first protocol may include at least one of a hyper text transfer protocol (HTTP), a transmission control protocol (TCP), or a file transfer protocol (FTP).

In some embodiments, the image data in the first format may include raw data acquired by the scan.

In some embodiments, the scan may correspond to a study instance unique identifier (UID), and the identification information of the image data may include the study instance UID.

In some embodiments, the operations may further include compressing the image data. The operations may further include determining index information of the compressed image data according to an identification generation algorithm. The index information may include a unique identification of the compressed image data. The operations may further include generating the metadata file based on the index information of the compressed image data, a file identifier of the compressed image data that indicates a format of the compressed image data, and the study instance UID. The identification information of the image data may further include the index information of the compressed image data and the file identifier of the compressed image data.

In some embodiments, the scan may further correspond to a series instance UID, and the identification information may further include the series instance UID.

In some embodiments, the image file to be transmitted also may include an original file in a third format. The original file may include the study instance UID and pixel data of one or more images generated based on the image data. The third format may include a standard Digital Imaging and Communications in Medicine (DICOM) format. The operations may further include transmitting, according to the second protocol, the original file to the image archiving system for archiving.

In some embodiments, the transmitting, according to a first protocol, the image data in the first format to an image archiving system for archiving may include compressing the image data; dividing the compressed image data into at least one sub-image data set; signing the at least one sub-image data set; and transmitting, according to the first protocol, the signed at least one sub-image data set to the image archiving system for archiving.

In some embodiments, the operations may further include causing the image archiving system to: store the image data according to an object storage service (OSS); determine an object storage index of the image data, the object storage index describing a storage path of the image data; and store a correlation relationship between the object storage index of the image data and index information of the image data of the metadata file for retrieving the image data. The index information of the image data may include a unique identification of the image data.

In some embodiments, the operations may further include receiving a search query, the search query including a target study instance UID corresponding to target data. The operations may further include obtaining, based on the search query, a target image file from the image archiving system.

The target image file may include at least one of a target metadata file or a target original file. The operations may further include identifying the target metadata file or the target original file in the target image file. The operations may further include obtaining, based on the identification result, the target data.

In some embodiments, the obtaining, based on the identification result, the target data may include in response to identifying the target metadata file in the target image file, obtaining target index information by parsing the target metadata file; obtaining, based on the target index information, target image data in the first format corresponding to the target index information from the image archiving system; and designating the target image data as the target data.

In some embodiments, the obtaining, based on the target index information, target image data in the first format corresponding to the target index information from the image archiving system may include transmitting, according to the first protocol, the target index information to the image archiving system; causing the image archiving system to search, based on the target index information, a target object storage index of the target image data from the image archiving system and retrieve, based on the target object storage index, the target image data; and obtaining, according to the first protocol, the target image data from the image archiving system.

In some embodiments, the obtaining, based on the identification result, the target data may include in response to identifying the target original file in the target image file, retrieving target pixel data in the second format from the target original file; and designating the target pixel data as the target data.

In some embodiments, the target image file may include a target file identifier of the target data, and the identifying the target metadata file or the target original file in the target image file may include identifying, based on the target file identifier of the target data, the target metadata file or the target original file in the target image file.

In another aspect of the present disclosure, a method implemented on a computing device including at least one storage device and at least one processor is provided. The method may include obtaining an image file to be transmitted that includes image data in a first format and a metadata file in a second format. The metadata file may include identification information of the image data. The image data may be acquired from a scan of a subject using an imaging device. The method may include transmitting, according to a first protocol, the image data in the first format to an image archiving system for archiving. The method may also include transmitting, according to a second protocol, the metadata file in the second format to the image archiving system for archiving.

In another aspect of the present disclosure, a non-transitory computer readable medium is provided. The non-transitory computer readable medium may include executable instructions that, when executed by at least one processor, direct the at least one processor to perform a method. The method may include obtaining an image file to be transmitted that includes image data in a first format and a metadata file in a second format. The metadata file may include identification information of the image data. The image data may be acquired from a scan of a subject using an imaging device. The method may include transmitting, according to a first protocol, the image data in the first format to an image archiving system for archiving. The method may also include transmitting, according to a second protocol, the metadata file in the second format to the image archiving system for archiving.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in descending order. However, the terms may be displaced by another expression if they achieve the same purpose.

Figure 2:
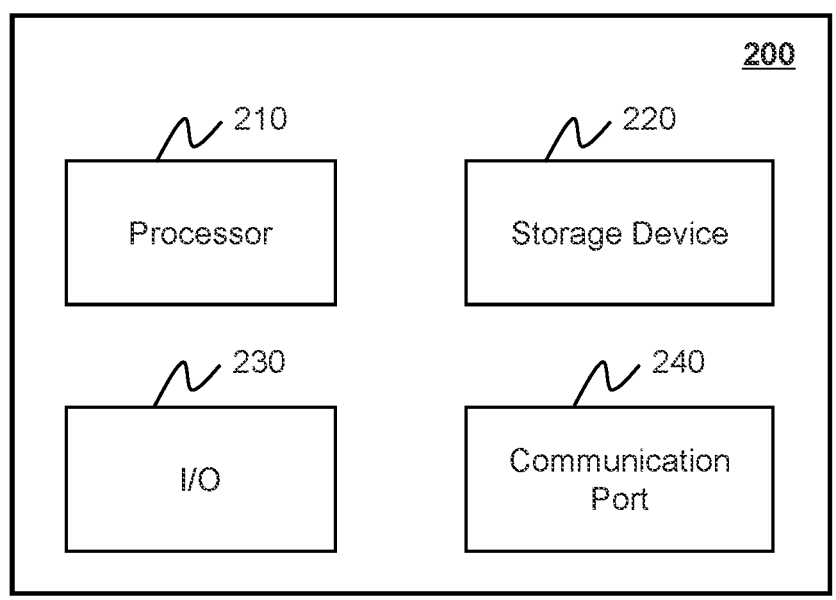
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image data" in the present disclosure is used to collectively refer to raw data (e.g., projection data) and/or images of various forms, including two-dimensional (2D) image data, three-dimensional (3D) image data, four-dimensional (4D) image data, etc. The terms "pixel" and "voxel" in the present disclosure are used interchangeably to refer to an element of an image. The subject may include a biological subject (e.g., a human, an animal), a non-biological subject (e.g., a phantom), etc. For example, the subject may include a specific part, organ, and/or tissue of a patient. As another example, the subject may include the head, the brain, the neck, the breast, the heart, the lung, the stomach, blood vessels, soft tissues, or the like, or any combination thereof. The term "object" or "subject" are used interchangeably in the present disclosure. The term "modality" used herein broadly refers to an imaging or treatment method or technology that gathers, generates, processes, and/or analyzes imaging information of a subject or treatments the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

An aspect of the present disclosure relates to systems and methods for file archiving and transmission. The systems and methods may obtain an image file to be transmitted that includes image data in a first format and a metadata file in a second format. The metadata file may include identification information of the image data. The image data (e.g., raw data) may be acquired from a scan of a subject using an imaging device. According to embodiments of the systems and methods described herein, the image data in the first format may be transmitted, according to a first protocol (also referred to as a proprietary file transmission protocol), an image archiving system (e.g., a PACS system) for archiving. According to embodiments of the systems and methods described herein, the metadata file in the second format may be transmitted, according to a second protocol (also referred to as a standard file transmission protocol), to the image archiving system for archiving.

Traditionally, the image archiving system (e.g., the PACS) generally supports archiving a file in a standard format (e.g., an image file including image(s) in a DICOM format) and does not support archiving a file in a non-standard format (e.g., an image file including raw dada associated with the image(s) in a format different from the DICOM format). The image archiving system cannot parse a file in a non-standard format. In some embodiments, even though the file in the non-standard format is transformed to a DICOM file (e.g., the file in the non-standard format being compressed to be stored in pixel data of the DICOM file), the size of the DICOM file may be too large to be reliably transmitted to and/or stored in the image archiving system since a transmission service (e.g., a C-type service such as C-Move, or C-Store) of DICOM may have a high risk of packet loss, which may result in file transmission failure.

According to some embodiments of the present disclosure, an image file including image data in a non-standard format and a relatively large size can be transmitted to the image archiving system for archiving according to a proprietary file transmission protocol, without being transformed to the standard format of the image archiving system. According to the proprietary file transmission protocol, the image data of the image file can be transmitted to the image archiving system reliably, avoiding or reducing the risk of packet loss during the transmission of the image file. Additionally, the metadata file may be in a self-defined format that is similar to the standard format except that the metadata file includes the identification information of the image data, instead of the image data itself. The metadata file can be transmitted to the image archiving according to the standard protocol for archiving. According to the metadata file, the image data can be queried and retrieved from the image archiving system conveniently. Further, an original file in the standard format may include image(s) generated based on image data (e.g., the raw data generated by the scan) and be transmitted to the image archiving system for archiving according to the standard protocol. The original file and the metadata file corresponding to the image data (e.g., the raw data of the scan) may be archived associatively by including the same unique identifier (UID) (e.g., the same study instance UID, or the same series instance UID) corresponding to the scan. Accordingly, the image data and the original file may be associated by a linkage between the original file and the metadata file and concurrently with a correlation between the metadata file and the image data, thereby facilitating a subsequent query of the image data and/or the original file from the image archiving system.

Figure 1:
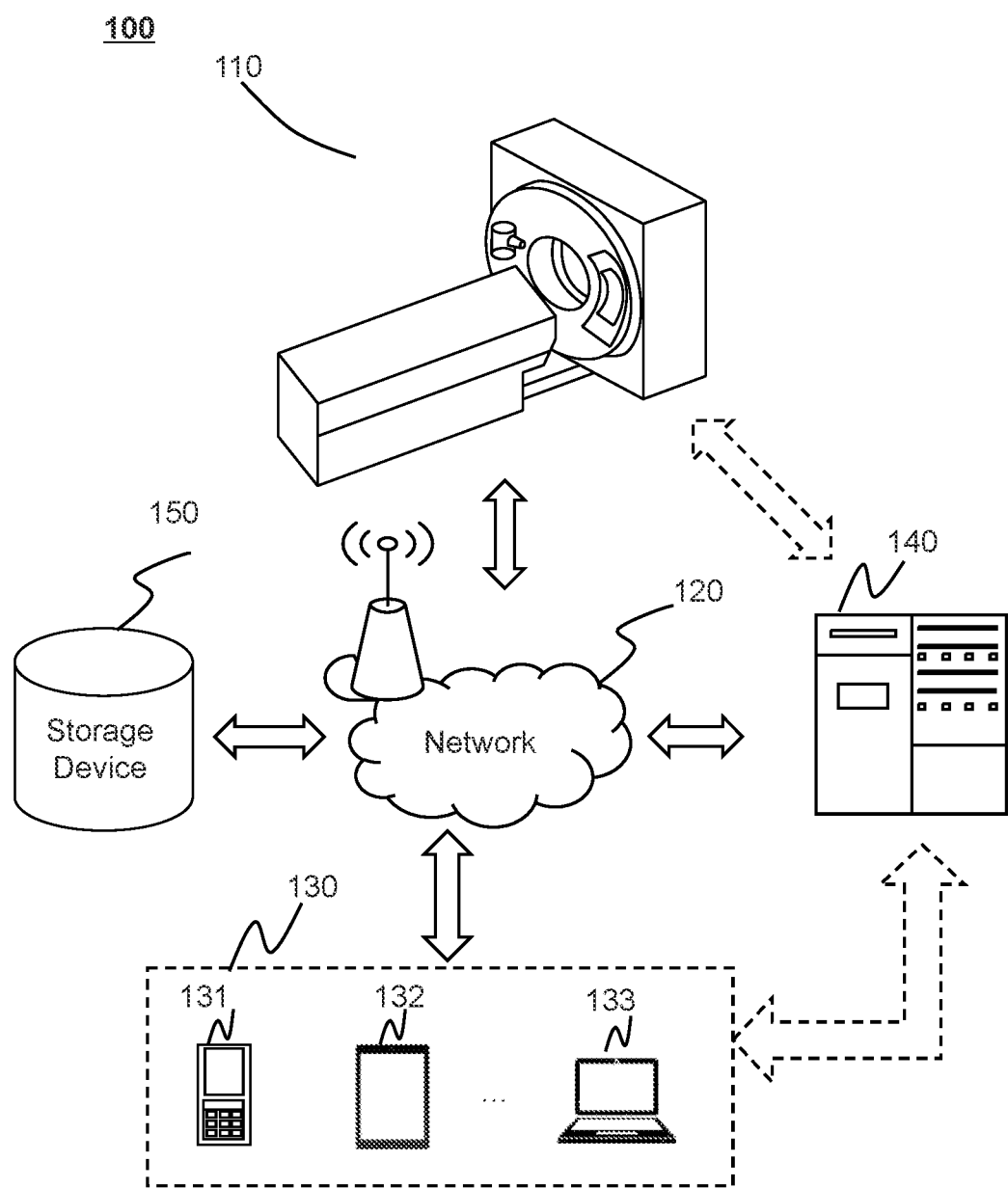
FIG. 1 is a schematic diagram illustrating an exemplary medical system according to some embodiments of the present disclosure.

FIG. 1 is a schematic diagram illustrating an exemplary medical system according to some embodiments of the present disclosure. In some embodiments, the medical system may be configured for non-invasive imaging, such as for disease diagnosis, treatment, and/or research purposes. In some embodiments, the medical system may include a single modality system and/or a multi-modality system. The single modality system may include an imaging system. Exemplary imaging systems may include a computed tomography (CT) system, a magnetic resonance imaging (MRI) system, a positron emission tomography (PET) system, a single-photon emission computed tomography (SPECT) system, a digital subtraction angiography (DSA) system, an X-ray system (e.g., a digital radiography (DR) system, an optical coherence tomography (OCT) imaging system, an ultrasound (US) imaging system, an intravascular ultrasound (IVUS) imaging system, a near-infrared spectroscopy (NIRS) imaging system (e.g., an infrared system), a microscopic system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a positron emission tomography-magnetic resonance imaging (PET-MRI) system, a digital subtraction angiography-magnetic resonance imaging (DSA-MRI) system, an image-guided radiotherapy (IGRT) system.

As shown in FIG. 1, the medical system 100 may include an imaging device 110, a network 120, a terminal device 130, a processing device 140, and a storage device 150. The components of the medical system 100 may be connected in one or more of various ways. Mere by way of example, as illustrated in FIG. 1, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The imaging device 110 may be configured to acquire/generate image data relating to a subject or a portion thereof. The image data may include raw data (e.g., projection data), an image (e.g., an image slice), etc., of the subject, or the portion thereof. For example, the imaging device 110 may scan the subject, or a portion thereof, that is located within its detection region and generate the raw data relating to the subject, or the portion thereof. The raw data may be processed (e.g., preprocessed and/or reconstructed) to generate image(s) of the subject, or the portion thereof. In some embodiments, the imaging device 110 may include a CT device, an MRI device, a PET device, a SPECT device, a DSA device, a DR device, an OCT imaging device, a US imaging device, an IVUS imaging device, a NIRS imaging device (e.g., an infrared device), a microscopic device, or the like, or any combination thereof. The following descriptions are provided with reference to the imaging device 110 being a CT device. It is understood that this is for illustration purposes and not intended to be limiting.

In some embodiments, the imaging device 110 may include a radiation source, a detector, a gantry, a table, etc. The radiation source and the detector may be mounted on the gantry. The subject may be placed on the table and moved to a scanning region of the imaging device 110. The radiation source may include a tube configured to emit radiation (e.g., X rays) traveling toward the subject. The detector may detect radiation (e.g., X-rays) emitted from the scanning region of the imaging device 110. In some embodiments, the detector may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

In some embodiments, after the imaging device 110 performs a scan of the subject or the portion thereof, the imaging device 110 may generate image data of the subject or the portion thereof. The image data of the subject or the portion thereof may need to be transmitted to an image archiving system (also referred to as a file system) for archiving. Image data and/or reports of the subject in a form of an electronic file may be transmitted digitally from/to the image archiving system, such that a user (e.g., an authorized user such as a doctor, a third party, etc.) can retrieve the image data for diagnosis and/or research purposes from the image archiving system. Merely by way of example, the image archiving system may include a picture archiving and communication system (PACS). The PACS may be a medical imaging technology configured to provide storage and access to image data from multiple modalities. In some embodiments, one or more components of the medical system 100 may be in communication with the image archiving system. For example, the processing device 140 may transmit the image data to the image archiving system for archiving via a wireless connection or a wired connection. After archiving, the processing device 140 may query and/or retrieve the image data from the image archiving system. In some embodiments, the image archiving system may be a part of the medical system 100. Alternatively, the image archiving system may be implemented on an external medical system or server (e.g., a cloud platform). More descriptions regarding the image archiving system may be found elsewhere in the present disclosure (e.g., FIG. 5 and the description thereof).

The processing device 140 may process data and/or information. The data and/or information may be obtained from the imaging device 110, the terminal(s) 130, and/or the storage device 150. For example, the processing device 140 may obtain an image file to be transmitted that includes image data in a first format and a metadata file in a second format. The metadata file includes identification information of the image data. The image data may be acquired from a scan of a subject using the imaging device 11. The processing device 140 may transmit, according to a first protocol, the image data in the first format to an image archiving system for archiving. The processing device 140 may transmit, according to a second protocol, the metadata file in the second format to the image archiving system for archiving. As another example, the processing device 140 may receive a search query. The search query may include a target study instance UID corresponding to target data. The processing device 140 may obtain, based on the search query, a target image file from the image archiving system. The target image file may include a target metadata file and/or a target original file. The processing device 140 may identify the target metadata file and/or the target original file in the target image file. The processing device 140 may obtain, based on the identification result, the target data.

In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal(s) 130, and/or the storage device 150 via the network 120. As another example, the processing device 140 may be directly connected to the imaging device 110, the terminal(s) 130, and/or the storage device 150 to access stored information and/or data. In some embodiments, the processing device 140 may be implemented on a cloud platform. For example, a cloud platform may include a private cloud, a public cloud, a hybrid cloud, a community cloud, a distributed cloud, an inter-cloud, and a multi-cloud, or the like, or any combination thereof. In some embodiments, the processing device 140 may be implemented by a computing device 200 having one or more components as illustrated in FIG. 2 or be a portion of the terminal 130.

The terminal 130 may input/output signals, data, information, etc. In some embodiments, the terminal 130 may enable user interaction with the processing device 140. For example, the terminal 130 may communicate with the processing device 140 and/or the image archiving system via the network 120. As another example, a user may access the image archiving system for data query via the terminal 130. For instance, the terminal 130 may obtain user input information (e.g., a search query) through an input device (e.g., a keyboard, a touch screen, a brain wave monitoring device), and transmit the input information to the processing device 140 for further processing. As still another example, the terminal 130 may display the image data of the subject on a display device (e.g., a screen of the terminal 130). The terminal 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, a pair of glasses, a helmet, a watch, clothing, a backpack, a smart accessory, or the like, or any combination thereof. In some embodiments, the mobile device may include a mobile phone, a personal digital assistant (PDA), a navigation device, a point of sale (POS) device, a laptop computer, a tablet computer, a desktop computer, or the like, or any combination thereof. In some embodiments, the virtual reality device and/or augmented reality device may include a virtual reality helmet, a pair of virtual reality glasses, a virtual reality patch, an augmented reality helmet, a pair of augmented reality glasses, an augmented reality patch, or the like, or any combination thereof. For example, the virtual reality device and/or augmented reality device may include a Google Glass™, an Oculus Rift™, a HoloLens™, a Gear VR™, or the like. In some embodiments, the terminal 130 may be part of the processing device 140. In some embodiments, the terminal 130 may be integrated with the processing device 140 as an operation station of the imaging device 110. Merely by way of example, a user/operator (for example, a doctor) of the medical system may control an operation of the imaging device 110 through the operation station.

The storage device 150 may store data (e.g., raw data of a subject), instructions, and/or any other information. In some embodiments, the storage device 150 may store data obtained from the imaging device 110, the terminal(s) 130 and/or the processing device 140. For example, the storage device 150 may store raw data of a subject obtained from the imaging device 110. In some embodiments, the storage device 150 may store data and/or instructions executed or used by the processing device 140 to perform exemplary methods described in the present disclosure. In some embodiments, the storage device 150 may include a mass storage device, a removable storage device, a volatile read-write memory, a read-only memory (ROM), or the like, or any combination thereof. For example, the mass storage device may include a magnetic disk, an optical disk, a solid-state drive, a mobile storage device, etc. The removable storage device may include a flash drive, a floppy disk, an optical disk, a memory card, a ZIP disk, a magnetic tape, etc. The volatile read-and-write memory may include a random access memory (RAM). The RAM may include a dynamic RAM (DRAM), a double date rate synchronous dynamic RAM (DDR-SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented by the cloud platform described in the present disclosure. For example, a cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the processing device 140, the terminal 130, etc.) of the medical system. One or more components of the medical system may access the data or instructions in the storage device 150 via the network 120. In some embodiments, the storage device 150 may be a part of the processing device 140 or may be independent and directly or indirectly connected to the processing device 140.

The network 120 may include any suitable network that can facilitate the exchange of information and/or data of the medical system. In some embodiments, one or more components of the medical system (e.g., the imaging device 110, the terminal 130, the processing device 140, the storage device 150, etc.) may communicate information and/or data with one or more components of the medical system via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, server computers, or the like, or a combination thereof. For example, the network 120 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 120 may include one or more network access points. For example, the network 120 may include wired and/or wireless network access points, such as base stations and/or Internet exchange points, through which one or more components of the medical system may be connected to the network 120 to exchange data and/or information.

It should be noted that the above description regarding the medical system is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical system may include one or more additional components and/or one or more components of the medical system described above may be omitted. In some embodiments, a component of the medical system may be implemented on two or more sub-components. Two or more components of the medical system may be integrated into a single component. In some embodiments, the medical system 100 may include a medical system other than an imaging system, such as a medical monitoring system for monitoring physiological information of a subject, or a portion thereof. For example, the medical system 100 may include an electrocardiograph (ECG) device that can generate an ECG image (e.g., in a Joint Picture Group (JPG) format). The image data may include an ECG image generated by the ECG device.

FIG. 2 is a schematic diagram illustrating exemplary hardware and/or software components of an exemplary computing device according to some embodiments of the present disclosure. The computing device 200 may be configured to implement any component of the medical system. For example, the imaging device 110, the terminal 130, the processing device 140, and/or the storage device 150 may be implemented on the computing device 200. Although only one such computing device is shown for convenience, the computer functions relating to the medical system as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal 130 and/or the storage device 150. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the imaging device 110, the terminal 130, the storage device 150, or any other component of the medical system. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth™ network, a Wi-Fi network, a WiMax network, a WLAN, a ZigBee™ network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
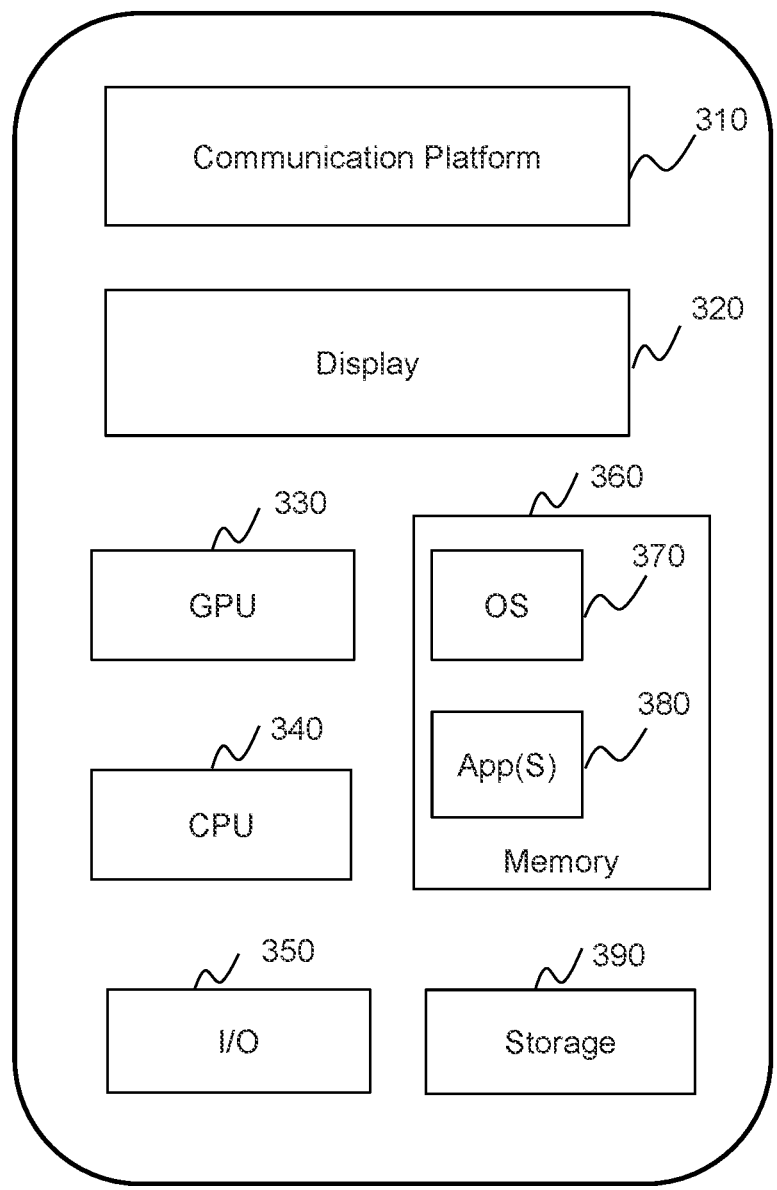
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the processing device 140 or the terminal 130 may be implemented on the mobile device 300.

As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the processor 210. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to imaging from the mobile device 300. User interactions with the information stream may be achieved via the I/O devices 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

Figure 4:
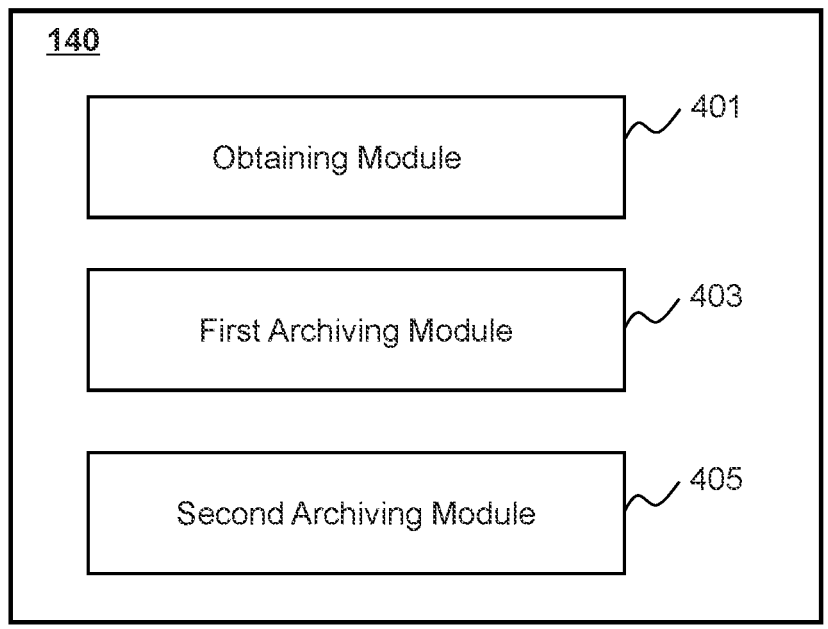
FIG. 4 is a block diagram illustrating an exemplary processing device according to some embodiments of the present disclosure.

FIG. 4 is a schematic diagram illustrating an exemplary processing device according to some embodiments of the present disclosure. As shown in FIG. 4, the processing device 140 may include an obtaining module 401, a first archiving module 403, and a second archiving module 405.

The obtaining module 401 may be configured to obtain, from one or more components of the medical system 100, data/information associated with file archiving, query, and/or retrieval. For example, the obtaining module 401 may obtain an image file from the storage device 150, the imaging device 110, and/or an imaging archiving system (e.g., a PACS) via the network 120. The image file may include image data in a first format (e.g., raw data in a non-standard format), a metadata file in a second format (e.g., a self-defined file in a self-defined DICOM format), an original file in a third format (e.g., a standard file in a standard DICOM format), or the like, or any combination thereof. As another example, the obtaining module 401 may obtain (e.g., generate) the metadata file based on the image data. More descriptions regarding the obtaining of the image file may be found elsewhere in the present disclosure (e.g., operation 501 in FIG. 1, FIG. 6, and the description thereof).

The first archiving module 403 may be configured to transmit the image data in the first format to the image archiving system for archiving. For example, the first archiving module 403 may transmit, according to a first protocol (e.g., a proprietary file transmission protocol), the image data to the image archiving system. The first archiving module 403 may cause the image archiving system to archive the image data. More descriptions of the transmission and/or the archiving of the image data may be found elsewhere in the present disclosure (e.g., operation 503 in FIG. 5, FIG. 7, and the descriptions thereof).

The second archiving module 405 may be configured to transmit the metadata file in the second format and/or the original file in the third format to the image archiving system for archiving. For example, the second archiving module 405 may transmit, according to a second protocol (e.g., a standard file transmission protocol), the metadata file and/or the original file to the image archiving system. The second archiving module 405 may cause the image archiving system to archive the metadata file and/or the original file. More descriptions of the transmission and/or the archiving of the metadata file and/or the original file may be found elsewhere in the present disclosure (e.g., operation 505 in FIG. 5 and the description thereof).

In some embodiments, the processing device 140 may include a querying module (not shown) configured for querying and/or retrieving target data (e.g., target image data in the first format and/or target original file in the third format). For instance, the querying module may include a query receiving unit, a file obtaining unit, a file parsing unit, and a file determination unit. The query receiving unit may be configured to obtain/receive a search query. The search query may include a target study instance UID and/or a target series instance UID corresponding to the target data. The file obtaining unit may be configured to obtain, from the image archiving system, a target standard file corresponding to the target study instance UID and/or the target series instance UID. The file parsing unit may be configured to, in response to identifying a target metadata file in the target image file, obtain target index information by parsing the target metadata file. The file determination unit may be configured to obtain, based on the target index information, target image data in the first format (e.g., the non-standard format) corresponding to the target index information from the image archiving system.

In some embodiments, the file determination unit may be divided into one or more sub-units, e.g., including an index transmission sub-unit and a file determination sub-unit. The index transmission sub-unit may be configured to transmit, according to the first protocol (e.g., a proprietary file transmission protocol), the index information to the image archiving system. The index transmission sub-unit may cause the image archiving system to search a target object storage index of the target image data from the image archiving system. The file determination sub-unit may be configured to obtain, based on the target object storage index, the target image data corresponding to the target index information.

In some embodiments, the querying module may also include a file identification unit configured to identify the target metadata file and/or the target original file in the target image file. In response to identifying the target metadata file in the target image file, the file parsing unit may obtain the target index information by parsing the target metadata file. In response to identifying the target original file in the target image file, the file determination unit may return to the target original file (e.g., obtain the target data from the target original file). In some embodiments, the querying module or a portion thereof may be a part of the obtaining module 401.

The modules in the processing device 140 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth™, a ZigBee™, a Near Field Communication (NFC), or the like, or any combination thereof. Each of the modules described above may be a hardware circuit that is designed to perform certain actions, e.g., according to a set of instructions stored in one or more storage media, and/or any combination of the hardware circuit and the one or more storage media. In some embodiments, the processing device 140 may include one or more additional modules, and/or one or more modules described above may be omitted from the processing device 140. For example, the processing device 140 may include a metadata file determination module configured to obtain/generate the metadata file. For instance, the metadata file determination module may include a first obtaining unit, a second obtaining unit, and a generation unit. The first obtaining unit may be configured to obtain compressed image data (e.g., by compressing the image data) and generate index information of the compressed image data. The second obtaining unit may be configured to obtain a file identifier of the compressed image data, the study instance UID of the compressed image data, the series instance UID of the compressed image data, or the like, or any combination thereof. The generation unit may be configured to generate the metadata file based on the index information, the file identifier, the study instance UID and/or the series instance UID (e.g., by storing the index information, the file identifier, the study instance UID and/or the series instance UID to a self-defined standard file). In some embodiments, the metadata file determination module may be a part of the obtaining module 401.

As another example, the querying module may be implemented on another processing device different from the processing device 140 in FIG. 4. Alternatively, the querying module may be a part of the obtaining module 401. That is, the function of the querying module or a portion thereof may be achieved by the obtaining module 401. As still another example, the processing device 140 may include a storage module (not shown) configured to store information and/or data (e.g., the target data) associated with the above-mentioned modules.

Additionally or alternatively, two or more modules may be integrated into a single module, and/or a module may be divided into two or more units. For example, the above-mentioned modules may be integrated into a console (not shown). Via the console, a user may archive and/or retrieve the target image data, etc. As another example, the second archiving module 405 may be divided into multiple units including, e.g., an obtaining unit for determining the at least one sub-image data, and a transmission unit for signing the at least one sub-image data and transmitting the signed at least one sub-image data to the image archiving system for archiving.

Figure 5:
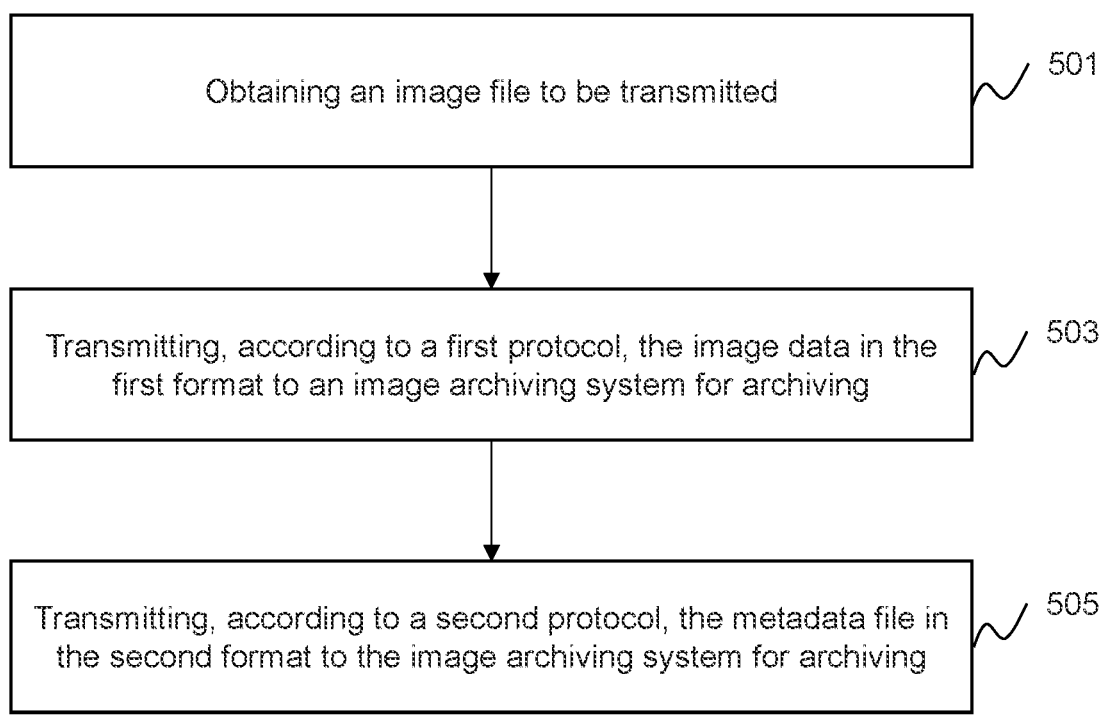
FIG. 5 is a flowchart illustrating an exemplary process for file archiving according to some embodiments of the present disclosure.

FIG. 5 is a flowchart illustrating an exemplary process for file archiving according to some embodiments of the present disclosure. In some embodiments, the process 500 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 501, the processing device 140 (e.g., the obtaining module 401) may obtain an image file to be transmitted. The image file may include image data in a first format and a metadata file in a second format.

In some embodiments, the first format may be a non-standard format. The second format may be a self-defined format. As used herein, a standard format refers to a default data format of an image archiving system. As used herein, a non-standard format refers to a format different from the standard format. A structure of the self-defined format may be similar to a structure of the standard format. The self-defined format may also be referred to as a self-defined standard format. Taking the image archiving system of the PACS as an example, the standard format may include a DICOM format, an Audio Video Interlevel (AVI) format, a Portable Document Format (PDF), etc. The non-standard format may include a binary format, e.g., a format identified by a file extension of at least one of ".ctr," ".ecg," ".hw," ".nc," ".raw," ".resp," ".sw," etc. Merely by way of example, the standard format includes the DICOM format, the first format may be a format different from the DICOM format, and the second format may be a self-defined DICOM format.

In some embodiments, the image data may be acquired and/or generated from a scan of a subject using an imaging device (e.g., the imaging device 110 such as an MRI device, a CT device, a US imaging device, an X-ray imaging device, an infrared device, a micrography device, or the like, or any combination thereof). For example, the image data may include raw data (e.g., the projection data) acquired by the scan, or a portion thereof, image(s) generated based on the raw data, or a portion thereof, preprocessed (e.g., filtered, denoised, artifact removed, labeled, etc.) raw data or image(s), or a portion thereof, or the like, or any combination thereof. For illustration purposes, the following description may be described with reference to the raw data, which is not intended to limit the scope of the present disclosure. For example, the image data in the first format may include raw data that is not in the DICOM format.

In some embodiments, taking the DICOM format as an example, the subject may correspond to a patient identifier (ID) (e.g., denoted by (0010, 0020)), profile information of the subject, etc. Different subjects may correspond to different patient IDs. The scan (also referred to as an examination) of the subject may correspond to a study instance unique identifier (UID) (e.g., denoted by (0020, 000D)). The study instance unique identifier may also be referred to as examination information. Different scans may correspond to different study instance UIDs. In some embodiments, the scan may correspond to one or more image sequences (also referred to as one or more image series). For example, the scan may include sub-scan(s) performed on different parts of the subject using the same imaging device 110. Each of the one or more image sequences may correspond to a part of the different parts of the subject. For instance, the one or more image sequences may include a first image sequence corresponding to the heart of the subject, and a second image sequence corresponding to the lung(s) of the subject. Each of the one or more image sequences may correspond to a series instance UID (e.g., including a sequence identifier, a sequence number, etc.) (e.g., 0020, 000E). Different image sequences may correspond to different series instance UIDs. In some embodiments, each of the one or more image sequences may include a plurality of image slices (or a plurality of images). Each of the plurality of image slices may be generated based on image data acquired according to a same scan (e.g., a same sub-scan). Each of the plurality of image slices may correspond to a service-object pair (SOP) instance UID (e.g., 0008, 0018)). Different image slices may correspond to different SOP instances UIDs. Accordingly, a scan may correspond to a patient ID and a study instance UID. The study instance UID may correspond to one or more series instance UID. Each of the one or more series instance UID may correspond to a plurality of SOP instance UIDs. Accordingly, the DICOM format may include multiple levels such as a first level of a subject ID (e.g., in the form of a patient ID), a second level of a study ID (in the form of, e.g., a study instance UID), a third level of a sequence ID (in a form of, e.g., a series instance UID), and a fourth level of an image ID (in a form of, e.g., a SOP instance UID). The first level, the second level, the third level, and the fourth level may be in descending order. That is, the subject may correspond to multiple studies, the study may correspond to multiple sequences, and the sequence may correspond to multiple images. In a file in the standard DICOM format, the contents of each layer (or level) of the file may conform to the configuration of the DICOM format. In a file in the self-defined DICOM format, the contents of each layer of the file may conform to the configuration of the DICOM format.

In some embodiments, the metadata file may include identification information of the image data, but not include the image data itself. The identification information of the image data may be configured for subsequent querying and/or retrieving of the image data from the image archiving system. The identification information may include a patient ID of the scan corresponding to the image data, the study instance UID of the scan corresponding to the image data, one or more series instance UIDs of the scan corresponding to the image data, a plurality of SOP instance UIDs corresponding to each of the one or more series instance UIDs, index information of the image data, a file identifier of the image data that indicates a format of the image data, or the like, or any combination thereof. As used herein, the index information of the image data refers to a unique identification of the image data generated based on the image data. The unique identification of the image data may include a sign bit, a timestamp that reflects a generation time of index information, an identifier of the image archiving system, a serial number of the index information, or the like, or any combination thereof. As used herein, the file identifier of the image data refers to identifier information of the image data itself. The identifier information of the image data may include a name of the image data, one or more keywords describing the contents of the image data, a type of the image data (e.g., a modality of the image data, the format of the image data, etc.), a size of the image data, a length of the image data, or the like, or any combination thereof. In some embodiments, the image data may include at least one sub-image data set, and the identifier information of the image data may include a count (or the number) of the at least one sub-image data set. In some embodiments, the file identifier of the image data may indicate a format of the metadata file. That is, the metadata file may be identified to be in the second format (e.g., a self-standard DICOM format) based on the file identifier of the image data.

In some embodiments, the image file may also include an original file in a third format, a file (e.g., a customized report) associated with the scan of the subject (e.g., which is produced by a user (e.g., a doctor, a researcher)), or the like, or any combination thereof. The third format may include the standard format such as a DICOM format (also referred to as a standard DICOM format). The original file may include original data and original identification information of the original data. The original data itself may be in the third format. The original data may include pixel data of one or more images (e.g., belonging to one or more image sequences) generated based on the image data. The identification information may include the patient ID of the scan, the study instance UID of the scan, one or more SOP instance UIDs corresponding to the one or more images respectively, a series instance UID corresponding to each of the one or more images, index information of the original file that indicates a format of the original file, a file identifier of the original file that indicates a format of the original file, a size of the original data, a count of the or more images of the original data, or the like, or any combination thereof.

In some embodiments, the metadata file in the self-defined format may be linked, based on linking information, to the original file in the third format. In some embodiments, the linking information may include at least one of the same patient UID, the same study instance UID, a same series instance UID, or a same SOP instance UID. That is, the original file may be associated with the metadata file. For example, the image data may be linked to all of the original data of the original file (i.e., the original data of the original file being generated based on the image data), and the metadata file may include a study instance UID of the original file. As another example, the image data may be linked to a part of the original data of the original file (e.g., an image sequence of the original data of the original file being generated based on the image data), and the metadata file may include a study instance UID of the original file and a series instance UID corresponding to the image sequence of the original file. Accordingly, the metadata file and the original file may be queried based on the linking information (e.g., the study instance UID, the series instance UID, etc.) of the metadata file and the original file.

In some embodiments, the processing device 140 may obtain the image file from one or more components of the medical system 100. For example, the processing device 140 may obtain the image file (e.g., the image data, the metadata file, and/or the original file) from a storage device (e.g., the storage device 150, the storage device 220, the storage 390, or an external device of the medical system 100, etc.). As another example, the processing device 140 may obtain the image data from the imaging device 110 or the storage device. The processing device 140 may obtain (or generate) the metadata file based on the image data, more descriptions of which may be found elsewhere in the present disclosure (e.g., FIG. 6 and the description thereof). As still another example, the original file may be pre-stored in the image archiving system. The processing device 140 may obtain the original file from the image archiving system for correlating the metadata file with the original file. In some embodiments, the processing device 140 may perform operation 501 according to a default setting of the medical system 100 (i.e., automatically) or in response to a request for archiving the image data. For example, the medical system 100 may be set to manage the image data in the image archiving system. In response to the imaging device 110 acquiring the image data, the processing device 140 may be triggered to automatically perform operation 501. As another example, the processing device 140 may be triggered to perform operation 501 when a request for archiving the image data is received from, e.g., a user.

In some embodiments, during an application of the PACS, a user of the medical system 100 may input and/or upload the image file to be transmitted to the processing device 140 (e.g., via the terminal 130). In response to receiving/obtaining the image file to be transmitted, the processing device 140 may identify format(s) of the image file, the processing device 140 may perform subsequent operations (e.g., operations 503, 505, etc.) for archiving based on the determined format(s) of the image file. For example, the processing device 140 may identify whether the image file includes a file in the first format (i.e., in the non-standard format), a file in the second format (i.e., in the self-standard format), and/or a file in the third format (i.e., in the standard format)). The processing device 140 may transmit files in different formats by invoking different transmission protocols of the image archiving system. In response to identifying the image file including the image data in the first format, the processing device 140 may proceed to perform operation 503. In response to identifying the image file includes the original file in the third format and/or the metadata file in the second format, the processing device 140 may proceed to operation 505. In this way, the files in different formats of the image file may be transmitted reliably and efficiently, thereby reducing or avoiding an error during the file transmission.

In 503, the processing device 140 (e.g., the first archiving module 403) may transmit, according to a first protocol, the image data in the first format to an image archiving system for archiving.

In some embodiments, the image archiving system may include one or more transmission interfaces. For example, the image archiving system may include a default transmission interface corresponding to a default transmission protocol (also referred to a standard file transmission protocol, or a second protocol). The image archiving system can transmit (receive and/or send) a file in the second format and/or the third format according to the second protocol via the default transmission interface. As another example, the image archiving system may include a proprietary transmission interface corresponding to a proprietary file transmission protocol (also referred to as the first protocol). The image archiving system can transmit (receive and/or send) a file in the first format according to the first protocol via the proprietary transmission interface. For example, the first protocol may include a proprietary file transmission protocol. Taking the PACS as an example, the first protocol may include at least one of a hyper text transfer protocol (HTTP or HTTP protocol), a transmission control protocol (TCP), or a file transfer protocol (FTP); the second protocol may include a DICOM protocol.

In some embodiments, the processing device 140 may invoke the first protocol of the image archiving system in response to identifying the image data in the first format in the image file. The processing device 140 may preprocess (by way of, e.g., compressing, dividing, signing, etc.) the image data in the first format. The processing device 140 may transmit, according to the first protocol, the preprocessed image data to the image archiving system. Alternatively, the processing device 140 may directly obtain the preprocessed image data in operation 501. The processing device 140 may transmit, according to the first protocol, the preprocessed image data to the image archiving system. More descriptions regarding the transmission of the image data in the first format may be found elsewhere in the present disclosure (e.g., FIG. 7 and the description thereof).

In 505, the processing device 140 (e.g., the second archiving module 405) may transmit, according to a second protocol, the metadata file in the second format to the image archiving system for archiving.

As described in operation 503, the second protocol may include a standard file transmission protocol (e.g., the DICOM protocol). In some embodiments, the processing device 140 may also transmit, according to the second protocol, the original file in the third format to the image archiving system for archiving. In response to identifying the metadata file in the second format and/or the original file in the third format in the image file, the processing device 140 may invoke the second protocol of the image archiving system. The processing device 140 may transmit, according to the second protocol, the metadata file and/or the original file to the image archiving system for archiving.

In some embodiments, the processing device 140 (e.g., the first archiving module 403 and/or the second archiving module 405) may cause the image archiving system to archive the image file (e.g., the image data, the metadata file, or, the original file, etc.). For example, in response to the image archiving system receiving the metadata file and/or the original file, the image archiving system may be caused (e.g., triggered) to perform the archiving of the metadata file and/or the original file. The image archiving system may store the metadata file and/or the original file in a first storage device of the image archiving system to complete archiving the metadata file and/or the original file. As another example, as described in connection with operation 503, in response to that the image archiving system receives the image data in the first format and/or the image archiving system has received the metadata file, the image archiving system may be caused (e.g., triggered) to perform the archiving operation of the image data. The image archiving system may store the image data in a second storage device of the image archiving system for completing the archiving the image data. That is, the image data and the metadata file an/or the original file may be stored in different storage devices, according to which the image data and the metadata file and/or the original file may be separately maintained. Further, by way of separately storing the image data and the metadata file and/or the original file, the image data may be compressed using a compression algorithm with a high compression ratio, thereby saving the amount of storage device the image data occupies. In some embodiments, the second storage device of the image archiving system and the first storage device of the image archiving system may be integrated into a same storage device. That is, the image data, the metadata file, and the original file may be stored in a same storage device of the image archiving system.

For instance, the image archiving system may store the image data (e.g., in the second storage device) according to an object storage service (OSS). The image archiving system may determine an object storage index of the image data. The object storage index may describe at least one of a storage path of the image data, a storage position of the image data, etc. The image archiving system may correlate the metadata file and the image data based on the object storage index for a subsequent query of the image data. For example, the image archiving system may store a correlation relationship between the object storage index of the image data and the index information of the image data of the metadata file for retrieving the image data. In some embodiments, the image archiving system may store the correlation relationship in the first storage device, the second storage device, or a third storage device of the image archiving system. For example, the correlation relationship may be stored in the first storage device the same as the metadata file and/or the original file. As another example, the correlation relationship may be stored in the second storage device the same as the image data. As still another example, the correlation relationship may be stored in the third storage device separately. In some embodiments, the image archiving system may store the correlation relationship in a correlation table (e.g., a dictionary table). The correlation table may include a plurality of correlation relationships corresponding to different image files stored in the image archiving system. Accordingly, the image archiving system may complete archiving the image data. More descriptions regarding the archiving of the image file may be found elsewhere in the present disclosure (e.g., FIG. 8 and the description thereof). In some embodiments, information of the image data such as the index information of the image data, the object storage index of the image data, etc. may also be referred to as access information of the image data. The metadata file may include the access information. In such cases, there is no need to generate the correlation relationship and/or store the correlation relationship, and the image data may be directly retrieved based on the object storage index of the image data, which improves the efficiency of the query and/or retrieval of the image data.

Traditionally, the image archiving system may not support the archiving of the image data in the non-standard format, and the image data may be stored in a storage disk separately other than the image archiving system. According to embodiments of the present disclosure, the image archiving system may be added to a transmission interface corresponding to a proprietary file transmission protocol. According to the proprietary file transmission protocol, the image archiving system may receive the image data in the non-standard format and store the image data using an SSO. In comparison with the traditional storage disk, by using the OSS, the efficiency of storing the image data may be improved, and the management of the image data may be more convenient. For example, additionally, the image archiving system may achieve, according to a standard file transmission protocol, the metadata file of the image data. Therefore, the image data may be located based on the correlation of the metadata file and the image data, which facilitates the query of the image data and improves the efficiency of the query.

According to some embodiments of the present disclosure, the image data may be transmitted, according to the first protocol (i.e., the proprietary file transmission protocol), to the image archiving system for archiving, thereby reducing or avoiding packet loss during the transmission and improving the reliability of the transmission. The identification information of the image data may be stored in the metadata file. The metadata file and/or the original file may be transmitted, according to the second protocol (i.e., the standard file transmission protocol), to the image archiving system for archiving. The metadata file may be correlated with the original file by including the same linking information (e.g., the study instance UID, the series instance UID, etc.). In this way, it is convenient for subsequently querying and/or retrieving, based on the linkage of the metadata file and the original file and/or the correlation between the metadata file and the image data, the image data from the image archiving system. More descriptions regarding querying and/or retrieving the image data may be found elsewhere in the present disclosure (e.g., FIGS. 9-12 and the descriptions thereof).

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added to or omitted from the process 500. For example, the process 500 may include an additional operation for causing the image archiving system to archive the image file (e.g., the image data, the metadata file, and/or the original file). As another example, a storing operation may be added elsewhere in the process 500. In the storing operation, the processing device 140 may store information and/or data used or obtained disclosed elsewhere in the present disclosure. As still another example, an additional operation may be added after operation 501 for identifying the format(s) of the image file. As further another example, an additional operation may be added to the process 500 for transmitting, according to the second protocol, the original file to the image archiving system for archiving. In some embodiments, an operation of the process 500 may be divided into at least two sub-operations. For example, operation 501 may be divided into two sub-operations, one of which is for obtaining the image data and the metadata file, and another one of which is for obtaining the original file. As still another example, operation 503 may be divided into two sub-operations, one of which is for preprocessing the image data, and another one of which is for transmitting the preprocessed image data to the image archiving system. In some embodiments, the metadata file may include a file identifier of the metadata file itself. The file identifier of the metadata file itself may directly indicate a format of the metadata file itself. For example, the filer identifier of the metadata file may indicate that the metadata file is in the second format (e.g., the self-defined DIOCM format). Similarly, the original file may include a file identifier of the original file itself. The file identifier of the original file itself may directly indicate a format of the original file.

Figure 6:
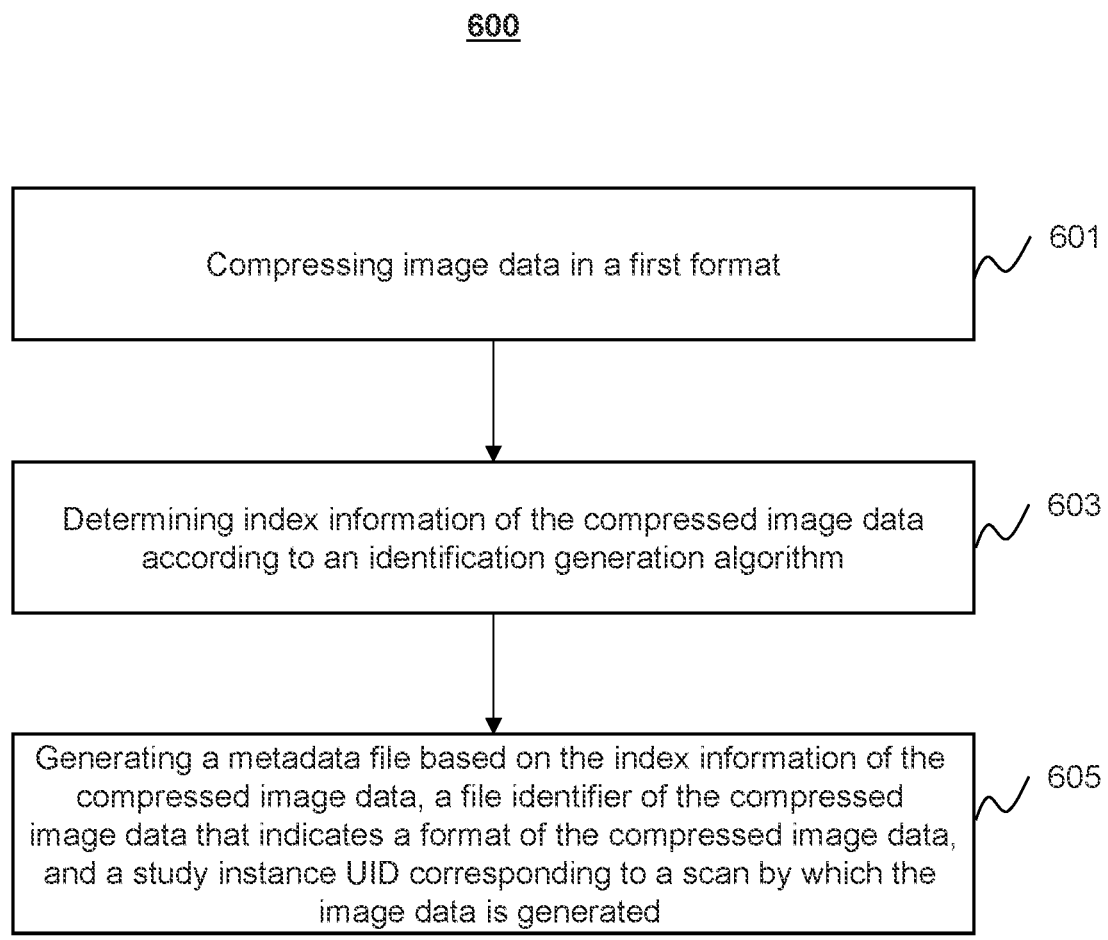
FIG. 6 is a schematic diagram illustrating an exemplary process for generating a metadata file according to some embodiments of the present disclosure.

FIG. 6 is a flowchart illustrating an exemplary process for generating a metadata file according to some embodiments of the present disclosure. In some embodiments, the process

600 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, at least part of operation 501 in FIG. 5 may be achieved by the process 600.

In 601, the processing device 140 (e.g., the obtaining module 401) may compress image data in a first format.

In some embodiments, the processing device 140 may compress the image data according to a compression algorithm. The compression algorithm may include a Huffman encoding algorithm, a run length encoding (RLE) algorithm, an arithmetic encoding algorithm, a dictionary decoding algorithm, or the like, or any combination thereof. In some embodiments, the processing device 140 may compress the image data until a size of the compressed image data is less than a threshold size. The threshold size may be a default setting of the medical system 100 or be self-defined by a user of the medical system.

In 603, the processing device 140 (e.g., the obtaining module 401) may determine index information of the compressed image data according to an identification generation algorithm.

In some embodiments, the index information may include a unique identification of the compressed image data. The unique identification of the compressed image data may include a sign bit, a timestamp that reflects a generation time of index information, an identifier of the image archiving system, a serial number of the index information, or the like, or any combination thereof. Different compressed image data may correspond to different index information, such that the index information of the compressed image data may be unique in the image archiving system. In some embodiments, the index information may be denoted by a string of numbers.

In some embodiments, the identification generation algorithm may include a snowflake algorithm, a universally unique identifier (UUID) algorithm, or the like, or any combination thereof.

In some embodiments, the processing device 140 may store the index information of the compressed image data as a private tag. The private tag may be used for querying the image data in the first format, more description of which may be found elsewhere in the present disclosure (e.g., FIGS. 9 and 10 and the descriptions thereof).

In 605, the processing device 140 (e.g., the obtaining module 401) may generate a metadata file based on the index information of the compressed image data, a file identifier of the compressed image data that indicates a format of the compressed image data, and a study instance UID of a scan by which the image data is generated.

In some embodiments, the processing device 140 may store the index information of the compressed image data, the file identifier (e.g., a format of the compressed image data) of the compressed image data, and the study instance UID in the metadata file. In some embodiments, the processing device 140 may store one or more of any other information (e.g., a patient UID, a series instance UID, an SOP instance UID, etc.) associated with the compressed image data in the metadata file. In some embodiments, the processing device 140 may generate the metadata file according to self-defined DICOM format, such that the metadata file can be transmitted according to the second protocol. As used herein, the self-defined DICOM format may be determined based on a standard DICOM format. A similarity between the self-defined DICOM format and the standard DICOM format may include that, the self-defined DICOM format includes index information of a file in the first format (i.e., the non-standard format such as a non-DICOM format), while the standard DICOM format includes index information of a file in the third format (i.e., the standard format such as the DICOM format). A difference between the self-defined DICOM format and the standard DICOM format may include that, the self-defined DICOM format does not include the file in the first format itself, while the standard DICOM format includes the file in the third format itself.

In some embodiments, the processing device 140 may obtain the file identifier of the compressed image data according to a user input. Alternatively, the processing device 140 may determine the file identifier by automatically identifying the compressed image data. In some embodiments, the processing device 140 may obtain the study instance UID, the series instance UID, etc., based on the scan and/or image sequences of the scan, more descriptions of which may be found elsewhere in the present disclosure (e.g., operation 501 and the description thereof).

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added to or omitted from the process 600. For example, operation 601 may be omitted from the process 600. As another example, an additional operation may be added before operation 605 for obtaining (or generating) the file identifier, the study instance UID, or the other information that may be included in the metadata file.

Figure 7:
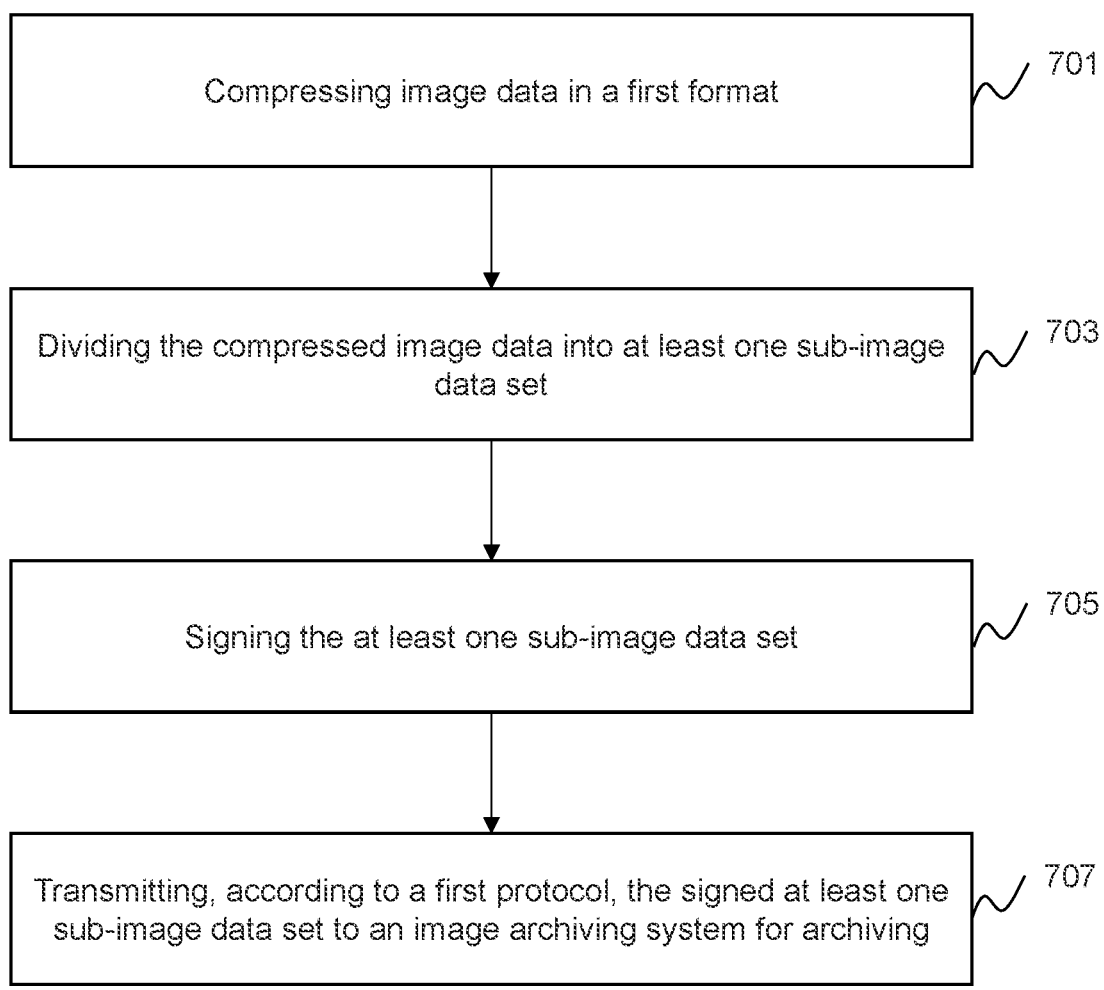
FIG. 7 is a flowchart illustrating an exemplary process for transmitting image data to an image archiving system for archiving according to some embodiments of the present disclosure.

FIG. 7 is a flowchart illustrating an exemplary process for transmitting image data to an image archiving system for archiving according to some embodiments of the present disclosure. In some embodiments, the process 700 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, at least part of operation 503 in FIG. 5 may be achieved by the process 700.

In 701, the processing device 140 (e.g., the first archiving module 403) may compress image data in a first format.

The processing device 140 may compress the image data in the first format according to a compression algorithm, which is similar to operation 601 and not repeated herein.

In 703, the processing device 140 (e.g., the first archiving module 403) may divide the compressed image data into at least one sub-image data set (also referred to as at least one data block).

In some embodiments, the processing device 140 may divide the compressed image data evenly. That is, each of the at least one sub-image data set may be of a same size. Alternatively, the processing device 140 may divide the compressed image data according to a preset size. The preset size may be a default setting of the medical system 100 or self-defined by a user of the medical system 100. In some embodiments, the processing device 140 may determine whether the compressed image data needs a division based on, e.g., the size of the compressed image data. In response to determining that the compressed image data needs a division, the processing device 140 may perform operation 703. For example, the processing device 140 may determine whether the compressed image data is relatively large for transmission (e.g., a size of the compressed image data exceeding a second threshold size). In response to determining that the compressed image data is relatively large for transmission, the processing device 140 may determine that the compressed image data needs a division.

In some embodiments, the processing device 140 may determine sub-index information (e.g., denoted by a string of numbers) of each of the at least one sub-image data set according to an identification generation algorithm, such that the sub-index information of each of the at least one sub-image data set may be unique in the image archiving system (i.e., the sub-index information being a globally unique identifier (GUID) for the corresponding sub-image data). The determination of the sub-index information may be similar to the determination of the index information of the compressed image data as described in operation 603 in FIG. 6 and is not repeated herein. Further, the processing device 140 may label each of the at least one sub-image data set with its corresponding sub-index information.

In 705, the processing device 140 (e.g., the first archiving module 403) may sign the at least one sub-image data set.

In some embodiments, the processing device 140 may sign the at least one sub-image data set (or the labeled at least one sub-image data set) using a signature algorithm (e.g., a message-digest algorithm 5 (MDA 5), a secure hash algorithm (SHA), a message authentication code (MAC) algorithm, etc.). For example, for each of the at least one sub-image data set (or the labeled at least one sub-image data set), the processing device 140 may generate a first signature (e.g., denoted by a first hash value) of the sub-image data (or the labeled sub-image data set) by using the signature algorithm. The processing device 140 may determine a signed sub-image data set based on the first signature. The signed sub-image data set may include the sub-image data set and the first signature of the sub-image data set.

In 707, the processing device 140 (e.g., the first archiving module 403) may transmit, according to a first protocol, the signed at least one sub-image data set to an image archiving system for archiving.

As described in connection with FIG. 5, the first protocol may be the proprietary file transmission protocol (e.g., the HTTP). In some embodiments, the proprietary file transmission protocol may be configured to support transfer control functions including, e.g., resumable data transfer, failed data rollback, or the like, or a combination thereof. The processing device 140 may transmit, according to the proprietary file transmission protocol, the at least one sub-image data set with at least one signature thereof to the image archiving system (e.g., the PACS). For example, the processing device 140 may transmit the at least one signed sub-image data set in sequence. As another example, the processing device 140 may transmit the at least one signed sub-image data in turn.

By dividing the compressed image data and transmitting the at least one sub-image data according to the proprietary file transmission protocol, the reliability of the transmission of relatively large data may be improved because the proprietary file transmission protocol supports transfer control functions including, e.g., resumable data transfer, failed data rollback, or the like, or a combination thereof.

In some embodiments, the processing device 140 may cause the image archiving system to verify the signed at least one sub-image data set. That is, in response to that the image archiving system receives the signed at least one sub-image data, the image archiving system may be caused (e.g., triggered) to verify the signed at least one sub-image data set based on the at least one signature of the at least one sub-image data. For example, for each of the signed at least one sub-image data set, the image archiving system may generate a second signature using the signature algorithm which is used to generate the signed sub-image data set. The image archiving system may verify the signed sub-image data by comparing the first signature of the signed sub-image data set and the second signature. In response to determining that the first signature is the same as the second signature, the image archiving system may verify that the signed sub-image data has data integrity. As another example, the image archiving system may verify whether the received signed sub-image data sets have duplicate first signatures. In response to verifying that the received signed sub-image data set(s) have duplicate first signatures, the image archiving system may keep one of the signed sub-image data sets that have the duplicate first signatures, thereby reducing or avoiding receipt of duplicate signed sub-image data sets. As still another example, the image archiving system may verify whether all of the signed at least one sub-image data set is received, thereby reducing or avoiding missing one or more signed sub-image data sets during transmission. After the verification of the signed at least one sub-image data set, the image archiving system may store, according to an object storage service (OSS), the signed at least one sub-image data set as a complete file in a storage device (e.g., the first storage device as described in operation 503) of the image archiving system for archiving. More description of the archiving process may be found elsewhere in the present disclosure (e.g., FIG. 5 and relevant description thereof).

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added to or omitted from the process 700. For example, a storing operation may be added elsewhere in the process 700. In the storing operation, the processing device 140 may store information and/or data used or obtained in operations of the process 700 in a storage device (e.g., the storage device 150) disclosed elsewhere in the present disclosure. As another example, the process 700 may further include an operation after 703 for determining the sub-index information of the at least one sub-image data set.

As still another example, operation 701 and/or operation 703 may be omitted. In some embodiments, the one or more operations of the process 700 may be integrated into an operation, and/or an operation of the process 700 may be divided into at least two sub-operations. For example, operations 701, 702, and/or 703 may be into a single operation.

Figure 8:
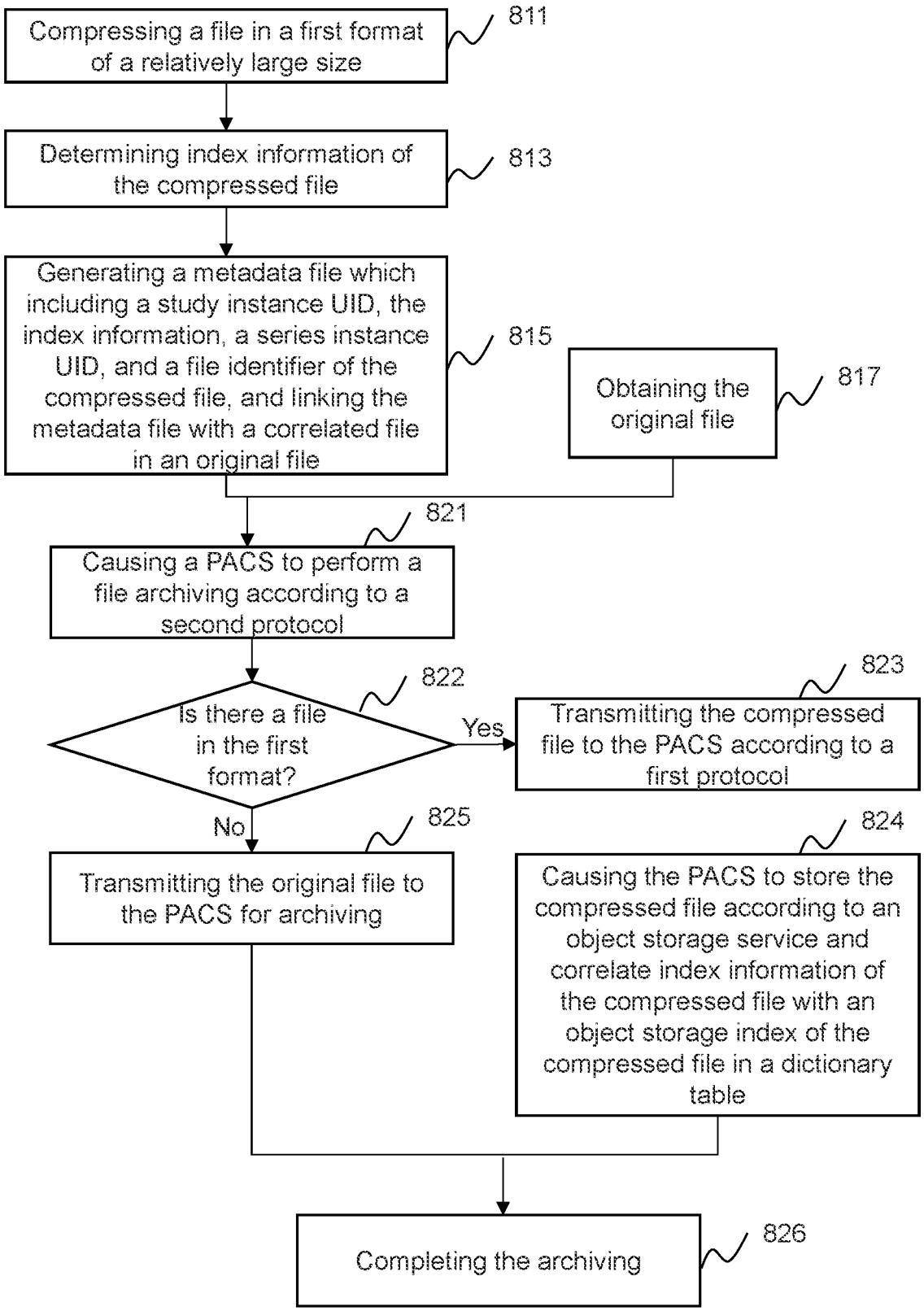
FIG. 8 is a flowchart illustrating an exemplary process for file archiving according to some embodiments of the present disclosure.

FIG. 8 is a flowchart illustrating an exemplary process for file archiving according to some embodiments of the present disclosure. In some embodiments, the process 800 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 811, the processing device 140 may compress a file in a first format (e.g., raw data in a non-standard format) of a relatively large size, which is similar to that described in operation 601 in FIG. 6.

In 813, the processing device 140 may determine index information of the compressed file, which is similar to that described in operation 603 in FIG. 6.

In 815, the processing device 140 may generate a metadata file (e.g., a self-defined file in a self-defined DICOM format) which includes a study instance UID, the index information, a series instance UID, and a file identifier of the compressed file. The processing device 140 may link the metadata file with a correlated file in an original file.

As used herein, the metadata file may be a self-defined standard file. The generation of the metadata file may be similar to that described in operation 605 in FIG. 6. The original file may include the same study instance UID and the same series instance UID as the metadata file. The correlated file in the original file may refer to a part of the original file, e.g., a file within the original file that corresponds to the series instance UID. The processing device 140 may link the metadata file with the correlated file based on the same series instance UID.

In 817, the processing device 140 may obtain the original file (e.g., in a standard DICOM format).

In 821, the processing device 140 may cause a PACS to perform a file archiving according to a second protocol (e.g., the standard file transmission protocol).

In some embodiments, when the processing device 140 intends to transmit a file for archiving, the processing device 140 may firstly trigger the second protocol of the PACS for archiving. Then, according to a determination result of operation 822, the processing device 140 may determine whether to trigger a first protocol (i.e., the proprietary file transmission protocol or the proprietary protocol) of the PACS.

In 822, the processing device 140 may determine whether there is a file in the first format.

In response to determining that there is a file in the first format, the processing device 140 may trigger the first protocol of the PACS and the process 800 may proceed to operation 823. In 823, the processing device 140 may transmit the compressed file to the PACS according to the first protocol, which is similar to that described in FIG. 7.

Also, the processing device 140 may transmit a metadata file of the compressed file to the PACD according to the second protocol and cause the PACS to archive the metadata file of the compressed file, which is similar to that described in operation 505 in FIG. 5. The metadata file may include index information of the compressed file.

In 824, the processing device 140 may cause the PACS to store the compressed file according to an object storage service (OSS) and correlate the index information of the compressed file with an object storage index of the compressed file in a dictionary table, more descriptions of which may be found elsewhere in the present disclosure (e.g., FIG. 5 and relevant description thereof).

In response to determining that there is no file in the first format, the process 800 may proceed to 825. In 825, the processing device 140 may transmit the original file to the PACS for archiving, more description of which may be found elsewhere in the present disclosure (e.g., FIG. 5 and relevant description thereof).

In 826, the processing device 140 may complete the archiving.

Figure 9:
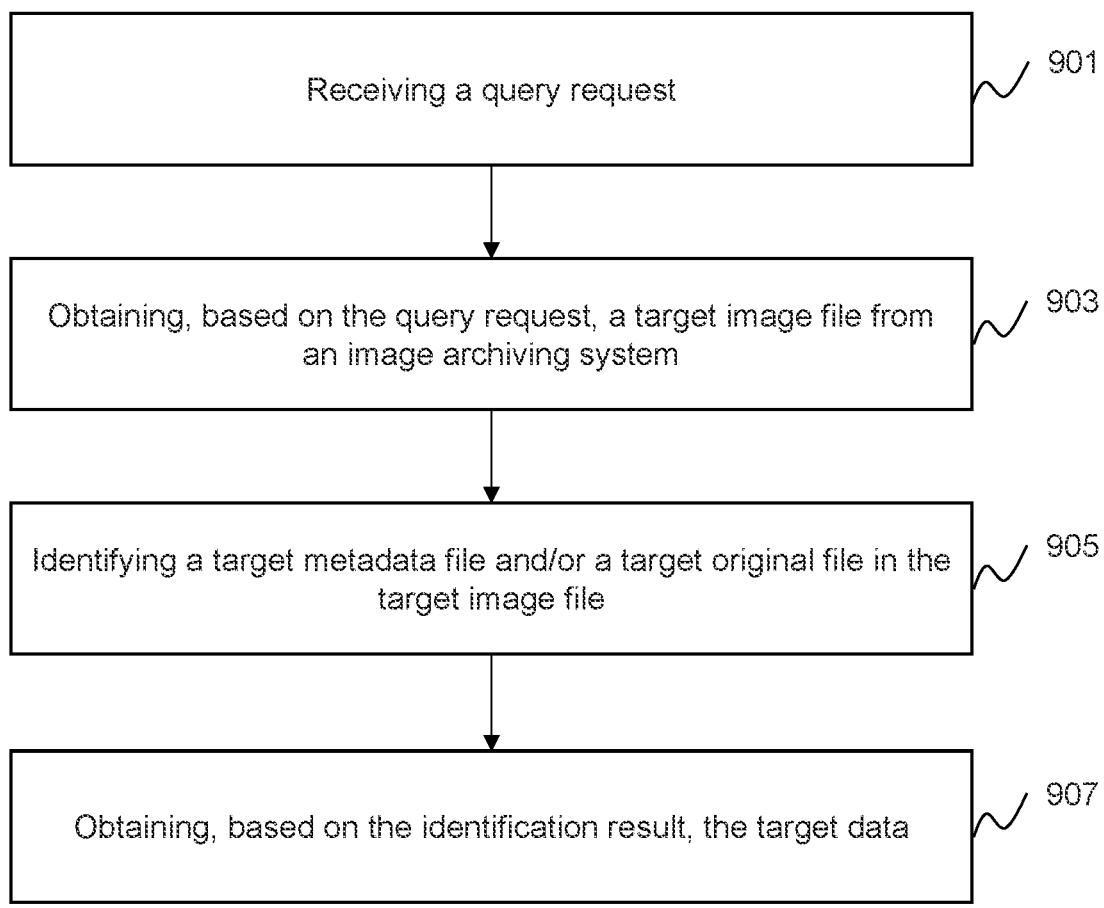
FIG. 9 is a flowchart illustrating an exemplary process for data query according to some embodiments of the present disclosure.

FIG. 9 is a flowchart illustrating an exemplary process for data query according to some embodiments of the present disclosure. In some embodiments, the process 900 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting. As described in connection with FIG. 5, after the archiving of the image file, the image file can be queried and/or retrieved from the image archiving system according to operations 901-907 of the process 900.

In 901, the processing device 140 (e.g., the obtaining module 401, or the querying module) may receive a search query.

In some embodiments, the processing device 140 may receive the search query according to a user input requesting target data.

In some embodiments, the search query may include one or more query conditions. Taking the PACS as an example, exemplary query conditions may include a target patient ID associated with the target data, a target modality of an imaging device associated with the target data, a target study instance UID corresponding to the target data, a target series instance UID corresponding to the target data, a target SOP instance UID corresponding to the target data, or the like, or any combination thereof. Merely by way of example, the search query may include the target study instance UID, the target series instance UID, and/or the patient UID.

In some embodiments, the processing device 140 (e.g., the obtaining module 401) may send, according to the second protocol (e.g., the standard file transmission protocol), the search query to the image archiving system by a standard query service of the image archiving system. Thus, the search query may be in the standard format (e.g., the third format), such that the search query may be transmitted to the image archiving system for data retrieval. Taking the PACS as an example, the standard query service may include a C-type query service (e.g., a C-Find service). The search query may be in the standard DICOM format. The processing device 140 may transmit the search query to the image archiving system by the C-Find service.

In 903, the processing device 140 (e.g., the obtaining module 401, or the querying module) may obtain, based on the search query, a target image file from the image archiving system.

In some embodiments, the processing device 140 may transmit, according to the second protocol, the search query to the image archiving system. The processing device 140 may cause the image archiving system to search, based on the search query, the target image file. In response to the image archiving system receiving the search query, the image archiving system may be caused or triggered to search the target image file by the standard query service. The image archiving system may obtain the target image file satisfying the query conditions of the search query. The image archiving system may transmit, according to the second protocol, the target image file to the processing device 140. Accordingly, the processing device 140 may obtain, according to the second protocol, the target image file from the image archiving system.

In some embodiments, the target image file may include at least one of a target metadata file or a target original file. For example, if the target metadata file and the target original file are pre-archived in the image archiving system, the image archiving system may obtain, based on the search query, both the target metadata file and the target original file. The image archiving system may transmit, according to the second protocol, the target metadata file and the target original file to the processing device 140. As another example, if only the target metadata file is archived in the image archiving system, the processing device 140 may obtain, according to the second protocol, the target metadata file from the image archiving system.

In 905, the processing device 140 (e.g., the obtaining module 401, or the querying module) may identify the target metadata file and/or the target original file in the target image file.

In some embodiments, the target image file may include one or more target file identifiers that indicate format(s) of file(s) in the target image file. The processing device 140 may identify, based on the target file identifiers, the target metadata file and/or the target original file in the target image file. Merely by way of example, the target image file may include a first file and a second file. The first file may include a first target file identifier, and the second file may include a second target file identifier. The processing device 140 may identify, based on the first target file identifier, that the first file is in a self-defined standard format. Accordingly, the processing device 140 may identify that the first file is the target metadata file in the target image file. Similarly, the processing device 140 may identify, based on the second target file identifier, that the second file is in a standard format. Accordingly, the processing device 140 may identify that the second file is the target original file in the target image file.

In 907, the processing device 140 (e.g., the obtaining module 401, or the querying module) may obtain, based on the identification result, the target data.

In some embodiments, the processing device 140 may obtain the target data based on the target original file and/or the target metadata file. For example, in response to identifying the target original file in the target image file, the processing device 140 may retrieve/obtain target pixel data in the standard format (i.e., the second format) from the target original file. The processing device 140 may designate the target pixel data as the target data. As another example, in response to identifying the target metadata file in the target image file, the processing device 140 may obtain target index information by parsing the target metadata file. The processing device 140 may obtain the target data (e.g., target image data in the first format) based on the target index information, more descriptions of which may be found elsewhere in the present disclosure (e.g., FIG. 10 and the description thereof). As still another example, in response to identifying the target original file and the target metadata file in the target image file, the processing device 140 may obtain the target data based on the target original file and the target metadata file.

It should be noted that the above description regarding the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added to the process 900 and/or omitted from the process 900. For example, the process 900 may also include a display operation. During the display operation, the processing device 140 may transmit the target data (e.g., the target pixel data and/or the target image data) to a terminal (e.g., the terminal 130) for displaying for the user.

Figure 10:
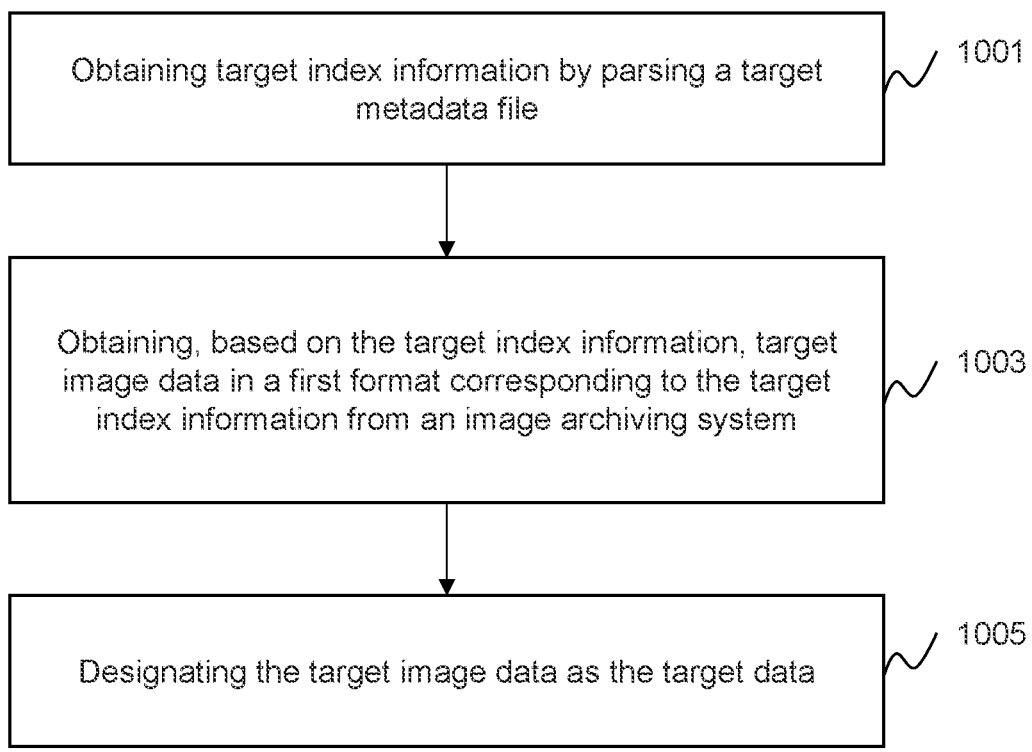
FIG. 10 is a flowchart illustrating an exemplary process for obtaining target data based on a target metadata file according to some embodiments of the present disclosure.

FIG. 10 is a flowchart illustrating an exemplary process for obtaining target data based on a target metadata file according to some embodiments of the present disclosure. In some embodiments, the process 1000 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 1000. The operations of the illustrated process presented below are intended to be illustrative. In some embodiments, the process 1000 may be accomplished with one or more additional operations not described and/or without one or more of the operations discussed. Additionally, the order of the operations of process 1000 illustrated in FIG. 10 and described below is not intended to be limiting. In some embodiments, at least part of operation 907 in FIG. 9 may be achieved by the process 1000.

In 1001, the processing device 140 (e.g., the obtaining module 401, or the querying module) may obtain target index information by parsing a target metadata file.

In 1003, the processing device 140 (e.g., the obtaining module 401, or the querying module) may obtain, based on the target index information, target image data in a first format (i.e., the self-defined standard format such as a self-defined DICOM format) corresponding to the target index information from an image archiving system.

In some embodiments, the processing device 140 may transmit, according to a second protocol (i.e., the standard file transmission protocol), the target index information to the image archiving system. The processing device 140 may cause the image archiving system to search, based on the target index information a target object storage index of the target image data from the image archiving system. The target object storage index may indicate a storage path and/or a storage position of the target image data. In response to the image archiving system receiving the target index information, the image archiving system may be caused or triggered to search the target object storage index. For example, the image archiving system may search the target object storage index in a correlation table (e.g., a dictionary table) which stores a correlation relationship between the target object storage index and the target index information. The correlation relationship between the target object storage index and the target index information may be stored in the correlation table when the target image data is being archived in the image archiving system. Further, the image archiving system may retrieve, based on the target object storage index, the target image data in a first format (i.e., the non-standard format). The image archiving system may transmit, according to the first protocol, the target image data to the processing device 140. Accordingly, the processing device 140 may obtain, according to the first protocol, the target image data from the image archiving system.

In 1005, the processing device 140 (e.g., the obtaining module 401, or the querying module) may designate the target image data as the target data.

According to some embodiments of the present disclosure, the querying of the target data may be achieved based on the archiving and/or storing information of the target data (e.g., the correlation relationship between the target index information and the target object storage index), which improves the accuracy and efficienly of the querying.

It should be noted that the above description regarding the process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added to the process 1000 and/or omitted from the process 1000.

Figure 11:
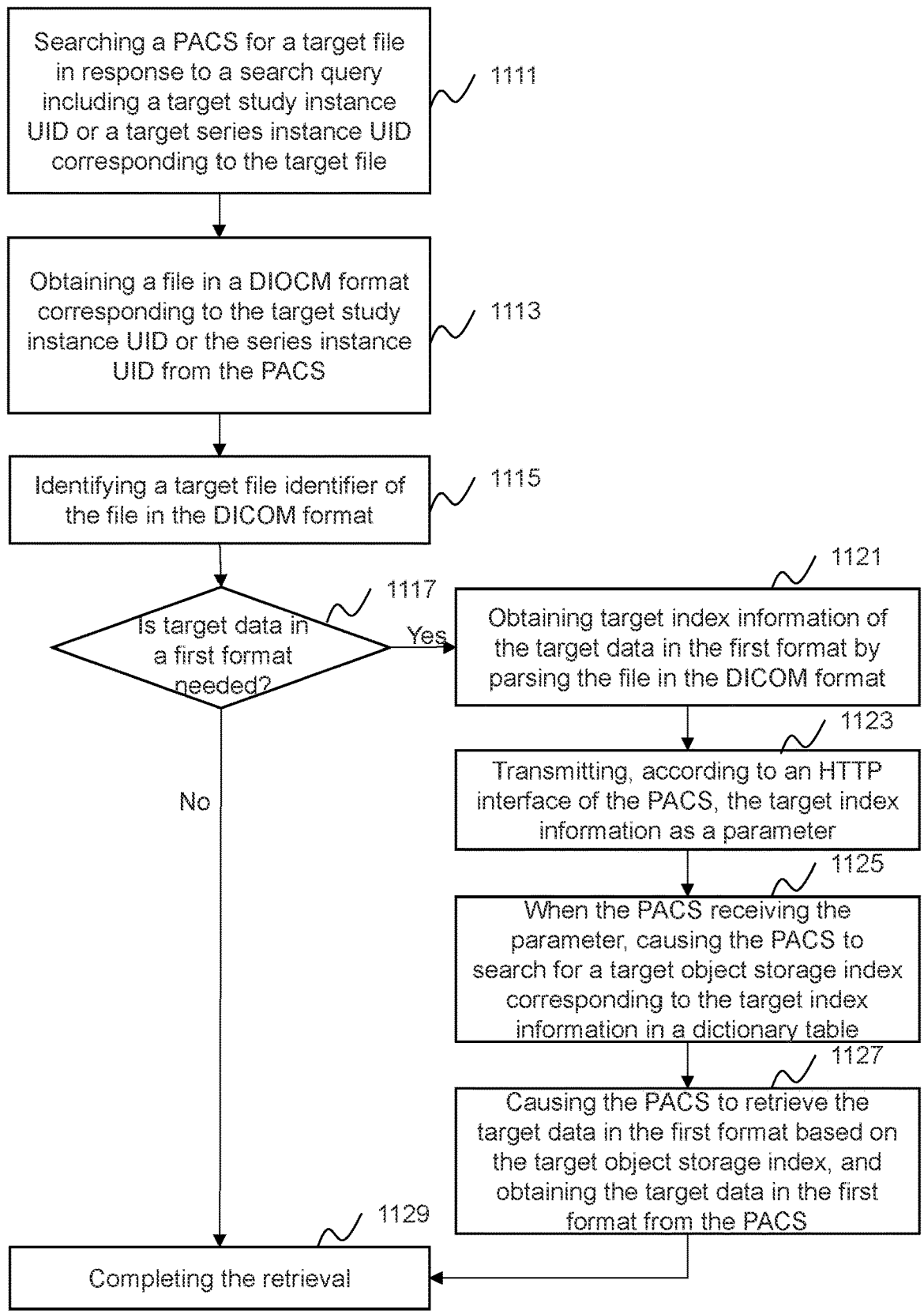
FIG. 11 is a flowchart illustrating an exemplary process for file query and retrieval according to some embodiments of the present disclosure.

FIG. 11 is a flowchart illustrating an exemplary process for file query and retrieval according to some embodiments of the present disclosure. In some embodiments, the process 1100 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 1100. The operations of the illustrated process presented below are intended to be illustrative. In some embodiments, the process 1100 may be accomplished with one or more additional operations not described and/or without one or more of the operations discussed. Additionally, the order of the operations of process 1100 illustrated in FIG. 11 and described below is not intended to be limiting.

In 1111, the processing device 140 may search a PACS for a target file in response to a search query including a target study instance UID or a target series instance UID corresponding to the target file. For example, the processing device 140 may transmit, according to the second protocol, a search query including the target instance UID or the target series instance UID to the PACS.

In 1113, the processing device 140 may obtain a file in a DIOCM format corresponding to the target study instance UID or the series instance UID from the PACS, which is similar to that described in operation 903 in FIG. 9. The file in the DICOM format may include at least one of a metadata file in a self-defined DICOM format and an original file in a standard DICOM format.

In 1115, the processing device 140 may identify a target file identifier of the file in the DICOM format. The target file identifier may indicate a format of the file in the DICOM format.

In 1117, the processing device 140 may determine whether target data in a first format (i.e., the non-standard format) is needed. For example, in response to identifying that the file in the DICOM format is in a self-defined DICOM format (indicating that the file is not an image file in the first format or the corresponding original image in the standard DICOM format), the processing device 140 may determine that the target data in the first format is needed. In response to identifying that the file in the DICOM format is in a self-defined DICOM format, the processing device 140 may determine that no target data in the first format is needed. Operation 1117 may be similar to operation 905.

In 1121, the processing device 140 may obtain target index information of the target data in the first format by parsing the file in the DICOM format, which is similar to that described in operation 1001 in FIG. 10.

In 1123, the processing device 140 may transmit, according to an HTTP interface of the PACS, the target index information as a parameter. For example, the processing device 140 may trigger the HTTP interface of the PACS. The processing device 140 may transmit, according to an HTTP protocol, the target index information as the parameter to the PACS, more descriptions of which may be found elsewhere in the present disclosure (e.g., operation 1003 in FIG. 10 and relevant description thereof).

In 1125, when the PACS receiving the parameter, the processing device 140 may cause the PACS to search for a target object storage index corresponding to the target index information in a dictionary table. The dictionary table may store a correlation relationship between the target object storage index and the target index information. The target object storage index may indicate a storage path and/or a storage position of the target data in the first format.

In 1127, the processing device 140 may cause the PACS to retrieve the target data in the first format based on the target object storage index, and proceed to 1129 when the retrieval is completed. The retrieval in 1127 may be similar to that described in operation 1005 in FIG. 10.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device including a set of instructions; and
at least one processor configured to communicate with the at least one storage device, wherein when executing the set of instructions, the at least one processor is configured to direct the system to perform operations including:

obtaining an image file to be transmitted;
in response to identifying that the image file includes image data in a first format, invoking a first protocol and transmitting, according to the first protocol, the image data in the first format to an image archiving system for archiving, wherein the first format includes a non-standard format, and the image data in the first format includes raw data that is acquired from a scan of a subject using an imaging device; and
in response to identifying that the image file includes a metadata file in a second format, invoking a second protocol and transmitting, according to the second protocol, the metadata file in the second format to the image archiving system for archiving, wherein the second format includes a self-defined Digital Imaging and Communications in Medicine (DICOM) format determined based on a standard DICOM format, and the metadata file in the second format includes identification information of the image data and does not include the image data.

2. The system of claim 1, wherein
the first protocol is a proprietary file transmission protocol, and
the second protocol is a standard file transmission protocol.

3. The system of claim 2, wherein the first protocol includes at least one of a hyper text transfer protocol (HTTP), a transmission control protocol (TCP), or a file transfer protocol (FTP).

4. The system of claim 1, wherein the scan corresponds to a study instance unique identifier (UID), and the identification information of the image data includes the study instance UID.

5. The system of claim 4, wherein the at least one processor is further configured to direct the system to perform the operations including:
compressing the image data;
determining index information of the compressed image data according to an identification generation algorithm, the index information including a unique identification of the compressed image data; and
generating the metadata file based on the index information of the compressed image data, a file identifier of the compressed image data that indicates a format of the compressed image data, and the study instance UID, wherein the identification information of the image data further includes the index information of the compressed image data and the file identifier of the compressed image data.

6. The system of claim 4, wherein the scan further corresponds to a series instance UID, and the identification information further includes the series instance UID.

7. The system of claim 4, wherein the image file to be transmitted also includes an original file in a third format, the original file including the study instance UID and pixel data of one or more images generated based on the image data, the third format including the standard DICOM format, and the operations further include:
transmitting, according to the second protocol, the original file to the image archiving system for archiving.

8. The system of claim 7, wherein the standard DICOM format includes index information of original file and the original file.

9. The system of claim 1, wherein the transmitting, according to a first protocol, the image data in the first format to an image archiving system for archiving includes:
compressing the image data;
dividing the compressed image data into at least one sub-image data set;
signing the at least one sub-image data set; and
transmitting, according to the first protocol, the signed at least one sub-image data set to the image archiving system for archiving.

10. The system of claim 9, wherein the signing the at least one sub-image data set includes:
for each of the at least one sub-image data set,
generating a signature of the sub-image data by using a signature algorithm; and
determining a signed sub-image data set based on the signature, the signed sub-image data set including the sub-image data set and the signature of the sub-image data set.

11. The system of claim 1, wherein the operations further include:
causing the image archiving system to
store the image data according to an object storage service (OSS);
determine an object storage index of the image data, the object storage index describing a storage path of the image data; and
store a correlation relationship between the object storage index of the image data and index information of the image data of the metadata file for retrieving the image data, the index information of the image data including a unique identification of the image data.

12. The system of claim 1, wherein the at least one processor is further configured to direct the system to perform the operations including:
receiving a search query, the search query including a target study instance UID corresponding to target data;
obtaining, based on the search query, a target image file from the image archiving system, the target image file including at least one of a target metadata file or a target original file; and
identifying the target metadata file or the target original file in the target image file; and
obtaining, based on the identification result, the target data.

13. The system of claim 12, wherein the obtaining, based on the identification result, the target data includes:
in response to identifying the target metadata file in the target image file,
obtaining target index information by parsing the target metadata file;
obtaining, based on the target index information, target image data in the first format corresponding to the target index information from the image archiving system; and
designating the target image data as the target data.

14. The system of claim 13, wherein the obtaining, based on the target index information, target image data in the first format corresponding to the target index information from the image archiving system includes:
transmitting, according to the first protocol, the target index information to the image archiving system;
causing the image archiving system to
search, based on the target index information, a target object storage index of the target image data from the image archiving system; and
retrieve, based on the target object storage index, the target image data, and
obtaining, according to the first protocol, the target image data from the image archiving system.

15. The system of claim 12, wherein the obtaining, based on the identification result, the target data includes:
   in response to identifying the target original file in the target image file,
      retrieving target pixel data in the second format from the target original file; and
      designating the target pixel data as the target data.

16. The system of claim 12, wherein the target image file includes a target file identifier of the target data, and the identifying the target metadata file or the target original file in the target image file includes:
   identifying, based on the target file identifier of the target data, the target metadata file or the target original file in the target image file.

17. The system of claim 1, wherein the at least one processor is configured to direct the system to perform operations including:
   in response to determining that the image archiving system receives the metadata file, causing the image archiving system to perform the archiving of the metadata file and store the metadata file in a first storage device of the image archiving system.

18. The system of claim 17, wherein the at least one processor is configured to direct the system to perform operations including:
   in response to determining that the image archiving system receives the image data in the first format and the image archiving system has received the metadata file, causing the image archiving system to perform the archiving of the image data and store the image data in a second storage of the imaging archiving system.

19. A method implemented on a computing device including at least one storage device and at least one processor, comprising:
   obtaining an image file to be transmitted;
   in response to identifying that the image file includes image data in a first format, invoking a first protocol and transmitting, according to the first protocol, the image data in the first format to an image archiving system for archiving, wherein the first format includes a non-standard format, and the image data in the first format includes raw data that is acquired from a scan of a subject using an imaging device; and
   in response to identifying that the image file includes a metadata file in a second format, invoking a second protocol and transmitting, according to the second protocol, the metadata file in the second format to the image archiving system for archiving, wherein the second format includes a self-defined Digital Imaging and Communications in Medicine (DICOM) format determined based on a standard DICOM format, and the metadata file in the second format includes identification information of the image data and does not include the image data.

20. A non-transitory computer readable medium, comprising executable instructions that, when executed by at least one processor, direct the at least one processor to perform a method, the method comprising:
   obtaining an image file to be transmitted;
   in response to identifying that the image file includes image data in a first format, invoking a first protocol and transmitting, according to the first protocol, the image data in the first format to an image archiving system for archiving, wherein the first format includes a non-standard format, and the image data in the first format includes raw data that is acquired from a scan of a subject using an imaging device; and
   in response to identifying that the image file includes a metadata file in a second format, invoking a second protocol and transmitting, according to the second protocol, the metadata file in the second format to the image archiving system for archiving, wherein the second format includes a self-defined Digital Imaging and Communications in Medicine (DICOM) format determined based on a standard DICOM format, and the metadata file in the second format includes identification information of the image data and does not include the image data.

* * * * *